(12) United States Patent
Downie et al.

(10) Patent No.: US 9,441,997 B2
(45) Date of Patent: Sep. 13, 2016

(54) METHOD OF, AND APPARATUS FOR, MEASURING THE PHYSICAL PROPERTIES OF TWO-PHASE FLUIDS

(71) Applicant: Air Products and Chemicals, Inc., Allentown, PA (US)

(72) Inventors: Neil Alexander Downie, Hampshire (GB); Jean Philippe Trembley, Surrey (GB)

(73) Assignee: AIR PRODUCTS AND CHEMICALS, INC., Allentown, PA (US)

( * ) Notice: Subject to any disclaimer, the term of this patent is extended or adjusted under 35 U.S.C. 154(b) by 0 days.

(21) Appl. No.: 14/402,452

(22) PCT Filed: May 23, 2013

(86) PCT No.: PCT/EP2013/060691
§ 371 (c)(1),
(2) Date: Nov. 20, 2014

(87) PCT Pub. No.: WO2013/174959
PCT Pub. Date: Nov. 28, 2013

(65) Prior Publication Data
US 2015/0096385 A1    Apr. 9, 2015

(30) Foreign Application Priority Data

May 24, 2012 (EP) .................................... 12169392

(51) Int. Cl.
*G01F 1/74*      (2006.01)
*G01F 1/86*      (2006.01)
(Continued)

(52) U.S. Cl.
CPC ............. *G01F 1/86* (2013.01); *G01F 1/3227* (2013.01); *G01F 1/74* (2013.01); *G01F 15/08* (2013.01);
(Continued)

(58) Field of Classification Search
CPC ........................................................ G01F 1/74
USPC ........................... 73/861.04, 861.27, 861.28
See application file for complete search history.

(56) References Cited

U.S. PATENT DOCUMENTS 3,561,832 A    2/1971   Karrer et al.
3,612,966 A    10/1971  Dybel
(Continued)

FOREIGN PATENT DOCUMENTS

CN    1240024        12/1999
CN    1287616 A      3/2001
(Continued)

OTHER PUBLICATIONS

Zeisel, D., H. Menzi and L. Ullrich, "A precise and robust quartz sensor based on tuning fork technology for (SF6)-gas density control", Sensors and Actuators 80, pp. 233-236 (2000).
(Continued)

*Primary Examiner* — Jewel V Thompson
(74) *Attorney, Agent, or Firm* — Larry S. Zelson

(57) ABSTRACT

There is provided a method of measuring the physical properties of a two-phase fluid using at least one piezoelectric oscillator immersed in the two-phase fluid, the two-phase fluid comprising a gas fraction and a liquid fraction, the method comprising: a) measuring the resonant frequency of the or each piezoelectric oscillator as a function of time; and b) determining, from the or each resonant frequency, at least one physical property of the two-phase fluid to characterize the two-phase fluid.

13 Claims, 16 Drawing Sheets

(51) Int. Cl.

| | | |
|---|---|---|
| *G01N 29/02* | (2006.01) | |
| *G01N 29/036* | (2006.01) | |
| *G01N 9/00* | (2006.01) | |
| *G01F 15/08* | (2006.01) | |
| *G01F 23/296* | (2006.01) | |
| *G01F 1/32* | (2006.01) | |

(52) U.S. Cl.
CPC ....... *G01F 23/2966* (2013.01); *G01F 23/2967* (2013.01); *G01N 9/002* (2013.01); *G01N 29/022* (2013.01); *G01N 29/036* (2013.01); *G01N 2009/004* (2013.01); *G01N 2009/006* (2013.01); *G01N 2291/014* (2013.01); *G01N 2291/024* (2013.01); *G01N 2291/02818* (2013.01)

(56) References Cited

U.S. PATENT DOCUMENTS

| | | |
|---|---|---|
| 3,635,084 A | 1/1972 | Lamphere |
| 3,902,355 A | 9/1975 | Weisser |
| 4,126,049 A | 11/1978 | Cotter |
| 4,168,624 A | 9/1979 | Pichon |
| 4,232,544 A | 11/1980 | Stansfeld |
| 4,272,982 A | 6/1981 | Arnold et al. |
| 4,275,393 A | 6/1981 | Johnston |
| 4,507,970 A | 4/1985 | Dinger |
| 4,526,480 A | 7/1985 | Ward |
| 4,644,796 A | 2/1987 | Ward |
| 4,644,804 A | 2/1987 | Ramm et al. |
| 4,680,970 A | 7/1987 | Ueda et al. |
| 4,713,774 A | 12/1987 | Funk et al. |
| 4,724,707 A | 2/1988 | Innerhofer |
| 4,734,609 A | 3/1988 | Jasmine |
| 4,741,213 A | 5/1988 | Hojoh |
| 4,747,311 A | 5/1988 | Hojoh |
| 4,835,456 A | 5/1989 | Liu |
| 4,881,412 A | 11/1989 | Northedge |
| 4,938,068 A | 7/1990 | Clements |
| 4,995,263 A | 2/1991 | Stocker |
| 5,136,885 A | 8/1992 | Liebermann et al. |
| 5,220,836 A | 6/1993 | Harms et al. |
| 5,235,844 A | 8/1993 | Bonne et al. |
| 5,307,668 A | 5/1994 | Vander Heyden |
| 5,307,683 A | 5/1994 | Phelps et al. |
| 5,421,190 A | 6/1995 | Brandle et al. |
| 5,471,882 A | 12/1995 | Wiggins |
| 5,594,181 A * | 1/1997 | Stange .................... G01F 1/662 73/861.27 |
| 5,659,129 A | 8/1997 | Asoyan et al. |
| 5,679,905 A | 10/1997 | Wardle et al. |
| 5,900,534 A | 5/1999 | Miller et al. |
| 5,954,089 A | 9/1999 | Seymour |
| 6,003,543 A | 12/1999 | Sulatisky et al. |
| 6,230,731 B1 | 5/2001 | Miller et al. |
| 6,266,996 B1 | 7/2001 | Livingston |
| 6,286,361 B1 | 9/2001 | Jones et al. |
| 6,532,822 B1 | 3/2003 | Boyd |
| 7,054,764 B2 | 5/2006 | Williams et al. |
| 7,444,878 B1 | 11/2008 | Pepples |
| 7,454,952 B2 | 11/2008 | Kita et al. |
| 2003/0053516 A1 | 3/2003 | Atherton |
| 2007/0068493 A1 | 3/2007 | Pavlovsky |
| 2007/0186982 A1 | 8/2007 | Cohen et al. |
| 2008/0184804 A1 | 8/2008 | Leverrier et al. |
| 2009/0151461 A1 | 6/2009 | Ishii |
| 2010/0107735 A1 | 5/2010 | Pavlovsky |
| 2010/0132471 A1 | 6/2010 | Hedtke et al. |
| 2010/0269365 A1 | 10/2010 | Miller et al. |
| 2011/0126930 A1 | 6/2011 | Hayashi et al. |
| 2012/0000559 A1 | 1/2012 | Mussot |
| 2012/0256086 A1 | 10/2012 | Husebo et al. |
| 2013/0042698 A1 | 2/2013 | Mayr et al. |
| 2015/0292922 A1* | 10/2015 | Downie .................... G01F 1/28 73/30.03 |
| 2015/0323359 A1* | 11/2015 | Ueberschlag .......... G01F 1/662 73/861.28 |

FOREIGN PATENT DOCUMENTS

| | | |
|---|---|---|
| CN | 1768312 A | 5/2006 |
| CN | 101708437 A | 5/2010 |
| CN | 101761779 A | 6/2010 |
| CN | 101881640 A | 11/2010 |
| CN | 202061563 U | 12/2011 |
| CN | 102472653 A | 5/2012 |
| CN | 202212112 U | 5/2012 |
| DE | 3345750 A1 | 6/1985 |
| DE | 3641842 A1 | 6/1988 |
| DE | 19901119 A1 | 7/2000 |
| DE | 10232823 A1 | 11/2003 |
| DE | 102010028475 A1 | 11/2011 |
| EP | 0101669 A2 | 2/1984 |
| EP | 0129753 A1 | 2/1985 |
| EP | 0273649 A2 | 7/1988 |
| EP | 0484569 A1 | 5/1992 |
| EP | 0582045 B1 | 5/1993 |
| EP | 0671680 A1 | 9/1995 |
| EP | 1930709 A1 | 11/2008 |
| GB | 1349256 A | 4/1974 |
| JP | 58151517 | 8/1983 |
| JP | 6010148 | 1/1985 |
| JP | 6434547 | 2/1989 |
| JP | 1170824 A | 7/1989 |
| JP | 3068828 A | 3/1991 |
| JP | 543044 | 2/1993 |
| JP | 09155180 A | 6/1997 |
| JP | 10010031 | 1/1998 |
| JP | 2002122498 A2 | 4/2002 |
| JP | 2004219386 A | 8/2004 |
| JP | 2004286514 A | 10/2004 |
| JP | 2005506495 | 3/2005 |
| JP | 2005241355 | 9/2005 |
| JP | 2006241516 A | 9/2006 |
| JP | 2007244946 A | 9/2007 |
| JP | 2009198472 A2 | 9/2009 |
| JP | 2010038867 A | 2/2010 |
| JP | 2015520853 A | 7/2015 |
| JP | 2015526653 A | 9/2015 |
| JP | 2015526694 A | 9/2015 |
| JP | 2015526695 A | 9/2015 |
| JP | 2015526773 A | 9/2015 |
| TW | M334632 Y | 6/2008 |
| TW | 201118290 | 6/2011 |
| TW | 201207339 | 2/2012 |
| WO | 9802686 A1 | 1/1998 |
| WO | 9940553 A1 | 8/1999 |
| WO | 2006084263 A2 | 8/2006 |
| WO | 2006107900 A2 | 10/2006 |
| WO | 2007002288 A2 | 1/2007 |
| WO | 2007050400 A1 | 5/2007 |
| WO | 2011039534 A1 | 4/2011 |
| WO | 2011138147 A1 | 10/2011 |

OTHER PUBLICATIONS

Trafag AG data sheets "8773 Density Sensor" (4 pp.) from 1999 (brochure date Apr. 1999).
"User handbook GMS gas monitor system", Riset AG, Schaffhausen (Switzerland), version of Jul. 6, 2001.
Boser, Niklaus MR., Affidavit of May 10, 2009, Riset, concerning the priority of the release of the user handbook of Nov. 6, 2001.
Tietze, U. and Schenk, Ch., "Semiconductor Circuit Technology", pp. 56-59 and pp. 354-357; fourth edition, SpringerVerlag Berlin Heidelberg New York, 1978.
Kuchling H., "Physik, Formein and Gesetze" [Physics, Formulae and Laws], pp. 164-169; 7th edition, Buch-und Zeit-Verlagsgesellschaft mbH Cologne, 1969.
Decision of the German Federal Patents Court in the matter 20 W (pat) 357/04, handed down on Oct. 12, 2009 and retrievable shortly

(56) References Cited

OTHER PUBLICATIONS thereafter on the internet on the home page of the German Federal Patents Court.
Density Sensor 8774 data sheet from Trafag AG, date Jan. 2006.
Suzuki et al., "GD Series Vibratory Gas Density Meters", Yokogawa Technical Report, 2000, No. 29.
European Patent Office, International Search Report of the International Searching Authority, mailed Jul. 18, 2013, for PCT/EP2013/060686.
European Patent Office, International Search Report of the International Searching Authority, mailed Aug. 2, 2013, for PCT/EP2013/060689.
European Patent Office, International Search Report of the International Searching Authority, mailed Jun. 18, 2013, for PCT/EP2013/060691.
Das, et al. "Flow Regime Identification in Cyrogenic Gas-Liquid Flow Through Vertical Tubes", Cryogenics, ( Kidlington, GB, Elsevier), Jun. 1, 1995, pp. 393-398, vol. 35. No. 6.
Zeisel et al.: "A Precise and Robust Quartz Senor Based on Turning Fork Technology for (SF6)—Gas Density Control", Sensors and Actuators, 2000, pp. 233-236, vol. 80.
Suzuki, Jun-ichi, "GD Series Vibratory Gas Density Meters", Yokogawa Technical Report English Edition, No. 29 (2000), pp. 23-26.
Sell, Johannes K., "Real-time monitoring of a high pressure reactor using a gas density sensor", Sensors and Actuators A: 162 (2010) 215-219.
Annex A: Documents cited in Opposition proceedings, included in letter from Beck Greener, Jun. 10, 2015.

\* cited by examiner

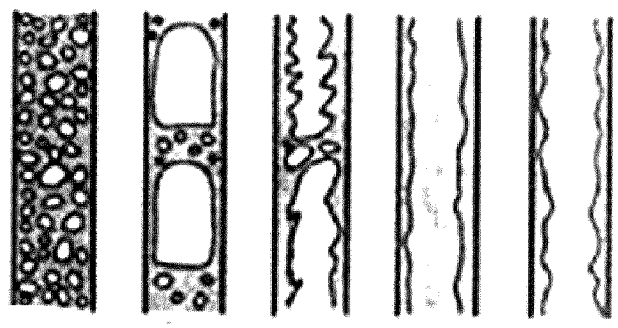
a) b) c) d) e) *Fig. 7*
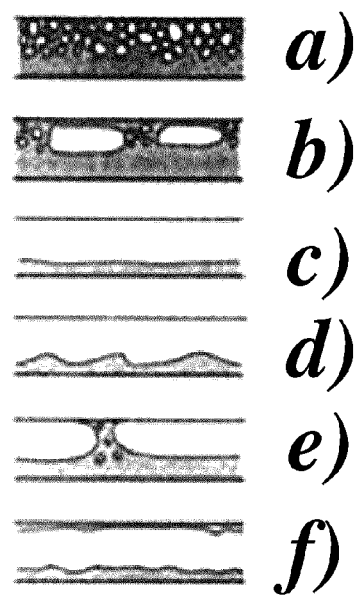
a)
b)
c)
d)
e)
f)
*Fig. 8*

METHOD OF, AND APPARATUS FOR, MEASURING THE PHYSICAL PROPERTIES OF TWO-PHASE FLUIDS

The present invention relates a method of, and apparatus for, measuring the physical properties of two-phase fluids. More particularly, the present invention relates to a method of, and apparatus for, measuring the physical properties of two-phase fluids using a piezoelectric oscillator.

Knowing the physical properties of a fluid—for example, the density or mass contents, rate of change of contents of fluid in a storage vessel, or mass flow rate of a fluid along a conduit has significant commercial application. This information is valuable both to the customer and the supplier of the fluid.

For gases, in many instances, it is necessary to monitor the contents of a given cylinder or pressure vessel to determine the amount of gas remaining. This is particularly critical in situations such as health care applications.

It is known to calculate, in accordance with the gas laws, the true contents of a cylinder from knowledge of the pressure of gas within a cylinder. Pressure measurement is a well known art and there are a variety of devices which function to measure pressure. The most conventional type uses an elastic diaphragm equipped with strain gauge elements. A common type of pressure gauge is a Bourdon gauge.

In the case of liquids, the most common measurement apparatus is a fill level gauge such as a float gauge. Alternatively, a particular type of float level gauge may be implemented which has a precise density and so is able to measure crudely the density of the liquid.

However, neither measurement technique is suitable for two-phase fluids, i.e. fluids comprising a liquid portion and a gas portion where a meniscus separates the two phases. In other words, where a gas fraction and a liquid fraction coexist within a particular volume of fluid. Cryogenic fluids commonly exist in two phase states.

Accurate measurement of the physical properties of a two-phase fluid is difficult using conventional techniques. This is because the examples discussed above are suitable to handle gas or liquid, but not both. In addition, cryogenic fluids present further measurement problems due to the low temperatures involved.

In addition, for many applications, it is desirable to know the mass flow rate of fluid from a storage vessel. This may be critical for many applications; for example, medical applications. A number of different mass flow meter arrangements are known.

A class of mass flow meters that are commonly used in many industrial applications are mechanical mass flow meters. Such meters include mechanical components which move or rotate to measure mass flow. One such type is the inertial flow meter (or coriolis flow meter) which measures fluid flow through the effect of the fluid on shaped tubes. Coriolis meters can handle a wide range of flow rates with high accuracy. However, in order to detect the flow rate, complex systems are required such as actuation, sensing, electronic and computational features.

Alternative mechanical-type mass flow meters are diaphragm meters, rotary meters and turbine meters. However, these types of meters are generally less accurate and involve moving parts which may be subject to wear. Further, meters such as rotary meters are only useful for measuring relatively low flow rates.

A further alternative class of mass flow meters are electronic flow meters. Two main types are thermal meters and ultrasonic meters. Thermal flow meters measure the heat transfer through a heated tube to measure flow rate. Ultrasonic flow meters measure the speed of sound in a gaseous medium, sometimes averaging the speed of sound over multiple paths within the pipe. However, both types of electronic flow meter generally require significant signal processing hardware and are generally high-cost items.

However, many known arrangements are unsuitable for use in cryogenic arrangements. Flow meters for cryogenic fluids are generally expensive and complicated devices. In addition, the accuracy of such devices often depends on the consistency of the gas and liquid fractions of the fluid. Many flow meters are accurate for subcooled and low gas fraction two phase flows (less than 0.5% gas by weight), but are poor for higher gas fraction two phase fluids, and gas only fluids. However, in cryogenic applications, the gas and liquid fractions in the fluid may vary greatly.

Known arrangements for cryogenic flow measurement generally operate by either measuring the flow directly using the velocity and density of the fluid, or measuring the flow indirectly using properties such as pressure drop and fluid modelling equations. Examples of flow meters that measure the flow directly are disclosed in U.S. Pat. No. 4,835,456, U.S. Pat. No. 3,635,084 and U.S. Pat. No. 4,272,982. In these arrangements, the flow is measured using a rotary element (such as a turbine) to derive fluid velocity directly. However, such arrangements are particularly vulnerable to variations in the gas and liquid fractions of the cryogenic fluid and can have poor accuracy if the flow regimes are subject to change or the proportions of gas to liquid vary or exceed particular levels.

Indirect measurement techniques include Pitot tubes, Venturi meters and orifice plate meters. These arrangements determine a pressure drop apply flow modelling equations, for example Bernoulli's equation, to the data. For two phase flow more complex flow modelling is required and is very dependent on the gas and liquid fractions of the cryogenic fluid. An example can be found in U.S. Pat. No. 4,168,624.

An alternative group of flow meters split the two-phase fluid into its gas and liquid phases and measure the flow rate of each phase. Examples of such flow meters are disclosed in U.S. Pat. No. 4,881,412 and U.S. Pat. No. 5,679,905. They are complex and expensive as they require two or more flow meters to measure the total flow.

An alternative arrangement is disclosed in U.S. Pat. No. 7,054,764. This arrangement measures the pressure and temperature of the two phase fluid, and performs an iterative calculation to determine mass flow.

An alternative type of device used to measure the physical properties of gases is a piezoelectric device such as a quartz crystal. Quartz crystals demonstrate piezoelectric behaviour, i.e. the application of voltage to them results in slight squeezing or stretching of the solid, and vice versa.

"*A Precise And Robust Quartz Sensor Based On Tuning Fork Technology For ($SF_6$)—Gas Density Control*" Zeisel et al, Sensors and Actuators 80 (2000) 233-236 discloses an arrangement whereby a quartz crystal sensor is used to measure the density of $SF_6$ gas in high and medium voltage electrical equipment at low gas pressures. The measurement of the density of the $SF_6$ gas is critical to the safety of the apparatus. This document describes a low pressure application for quartz sensor technology in which pressures of up to 8 bar g are used.

U.S. Pat. No. 4,644,796 discloses a method and apparatus for measuring the pressure of a fluid using a quartz crystal oscillator housed within a variable-volume housing comprising a bellows arrangement. The internal volume of the housing varies due to compression/expansion of the bellows by external fluid pressure. Consequently, the density of the fluid within the housing varies as the internal volume of the housing varies. The density within the housing can be measured using a quartz crystal oscillator.

The above arrangements describe the use of a solid state sensor such as a quartz crystal oscillator. However, neither of the above arrangements and methods is suitable for accurately measuring the properties of a two-phase fluid or a cryogenic liquid.

According to a first aspect of the present invention, there is provided a method of measuring the physical properties of a two-phase fluid flow using at least one piezoelectric oscillator immersed in the two-phase fluid, the two-phase fluid comprising a gas fraction and a liquid fraction dispersed within a particular volume of fluid, the method comprising: a) measuring the resonant frequency of the or each piezoelectric oscillator as a function of time; and b) determining, from the or each resonant frequency, whether the or each piezoelectric oscillator is immersed in a gas fraction or a liquid fraction and determining therefrom the proportion of the gas fraction to the liquid fraction as a function of time to characterise the two-phase fluid.

According to an embodiment, there is provided a method of measuring the physical properties of a two-phase fluid using at least one piezoelectric oscillator immersed in the two-phase fluid, the two-phase fluid comprising a gas fraction and a liquid fraction, the method comprising: a) measuring the resonant frequency of the or each piezoelectric oscillator as a function of time; and b) determining, from the or each resonant frequency, at least one physical property of the two-phase fluid to characterise the two-phase fluid.

In one embodiment, step b) comprises determining whether the or each piezoelectric oscillator is immersed in a gas fraction or a liquid fraction based on said resonant frequency.

In one embodiment, the method further comprises comparing the resonant frequency with a pre-determined threshold frequency to determine whether said piezoelectric oscillator is immersed in a gas fraction or a liquid fraction.

In one embodiment, at least one physical property comprises the proportion of the gas fraction to the liquid fraction as a function of time.

In one embodiment, at least one physical property comprises the density of at least the liquid component of the two-phase fluid.

In one embodiment, the method further comprises the steps of: c) measuring the volumetric flow rate of the fluid; and d) determining the mass flow rate of the two-phase fluid from the proportion of the gas fraction to the liquid fraction and from the density of the liquid fraction.

In one embodiment, at least one physical property is the frequency of detection of a gas fraction and/or the size of a gas fraction.

In one embodiment, the frequency of detection of a gas fraction and/or the size of a gas fraction is used to determine the flow regime of said two-phase fluid.

In one embodiment, the frequency of detection of a gas fraction and/or the size of a gas fraction is used to determine whether said two-phase fluid is boiling.

According to a second aspect of the present invention, there is provided a sensor assembly for measuring the physical properties of two-phase fluid flow comprising a gas fraction and a liquid fraction dispersed within a particular volume of fluid, the sensor assembly comprising at least one piezoelectric oscillator for immersion in the two phase fluid, the sensor assembly being arranged to measure the resonant frequency of the piezoelectric oscillator as a function of time, to determine, from the resonant frequency, whether the or each piezoelectric oscillator is immersed in a gas fraction or a liquid fraction and to determine therefrom the proportion of the gas fraction to the liquid fraction as a function of time to characterise the two-phase fluid.

According to an embodiment, there is provided a sensor assembly for measuring the physical properties of a two-phase fluid comprising a gas fraction and a liquid fraction, the sensor assembly comprising at least one piezoelectric oscillator for immersion in the two phase fluid, the sensor assembly being arranged to measure the resonant frequency of the piezoelectric oscillator as a function of time and to determine, from the resonant frequency, at least one physical property of the two-phase fluid to characterise the two-phase fluid.

In one embodiment, the sensor assembly comprises a plurality of piezoelectric oscillators.

In one embodiment, said plurality of piezoelectric oscillators are arranged about the interior of a conduit through which said two-phase fluid is operable to flow.

In one embodiment, the sensor assembly is further operable to determine whether the piezoelectric oscillator is immersed in a gas fraction or a liquid fraction by comparing the resonant frequency with a pre-determined threshold frequency.

In one embodiment, at least one physical property comprises the proportion of the gas fraction to the liquid fraction as a function of time and/or the density of at least the liquid component of the two-phase fluid.

In one embodiment, the sensor assembly further comprises a flow meter operable to determine the volumetric flow rate of the two-phase fluid, the mass flow meter being operable to determine the mass flow rate of the two-phase fluid from the proportion of the gas fraction to the liquid fraction and from the density of the liquid fraction.

In one embodiment, the two-phase fluid is a cryogenic fluid.

In one embodiment, the two-phase fluid is stored in a storage tank and the density of the fluid is used to determine whether stratification is taking place in the storage tank.

In one embodiment, step a) comprises: driving, by means of a drive circuit, the piezoelectric oscillator such that the piezoelectric oscillator resonates at a resonant frequency; and measuring said resonant frequency over a pre-determined time period.

In one embodiment, said piezoelectric oscillator comprises a quartz crystal oscillator.

In an embodiment, the quartz crystal comprises at least one tine. In a variation, the quartz crystal comprises a pair of planar tines.

In an embodiment, the quartz crystal is AT cut or SC cut.

In a variation, the surface of the quartz crystal is directly exposed to the fluid.

In one embodiment, the sensor assembly comprises a drive circuit. In a variation, the sensor assembly comprises a drive circuit comprising a Darlington pair arranged in a feedback configuration from a common emitter amplifier.

In one embodiment, the sensor assembly comprises a power source. In one arrangement, the power source comprises a lithium-ion battery.

In one embodiment, the sensor assembly comprises a processor.

In a variation, said piezoelectric oscillator comprises a quartz crystal oscillator.

In a variation, the gas is a permanent gas.

In one arrangement, the high-pressure vessel is a gas cylinder.

In an embodiment, the sensor assembly comprises a drive circuit. In an embodiment, the sensor assembly comprises a drive circuit comprising a Darlington pair arranged in a feedback configuration from a common emitter amplifier.

In one embodiment, the sensor assembly comprises a power source. In one arrangement, the power source comprises a lithium-ion battery.

In one embodiment, the sensor assembly comprises a processor.

In one embodiment, the sensor assembly is arranged to drive the piezoelectric oscillator such that the piezoelectric oscillator resonates at a resonant frequency and to measure said resonant frequency over a pre-determined time period to determine the density of gas.

In one embodiment, the sensor assembly comprises a drive circuit. In one embodiment, the sensor assembly comprises a power source. In a variation, the power source comprises a lithium-ion battery.

According to an embodiment, there is provided a method of measuring the physical properties of a cryogenic fluid within a storage vessel using at least one piezoelectric oscillator immersed in the cryogenic fluid within the storage vessel, the method comprising: a) measuring the resonant frequency of the or each piezoelectric oscillator; and b) determining, from the or each resonant frequency, the density of the cryogenic fluid within the storage vessel.

In one embodiment, the method further comprising using a plurality of piezoelectric oscillators immersed at different levels in the cryogenic fluid to determine the density of the cryogenic fluid at different levels within the storage vessel.

In one embodiment, the method further comprises the step of: c) determining, based on said density measurements, the fluid level within the storage vessel.

In one embodiment, the method further comprises the step of: d) determining, based on said density whether stratification is taking place in the storage vessel.

According to an embodiment, there is provided a sensor assembly for measuring the physical properties of a cryogenic fluid within a storage vessel, the sensor assembly comprising at least one piezoelectric oscillator arranged to be immersed in the cryogenic fluid within the storage vessel, the sensor assembly being arranged to measure the resonant frequency of the or each piezoelectric oscillator and to determine, from the or each resonant frequency, the density of the cryogenic fluid within the storage vessel.

In one embodiment, the sensor assembly comprises a plurality of piezoelectric oscillators arranged at different levels within the storage vessel and operable to determine the density of the cryogenic fluid at different levels within the storage vessel.

In one embodiment, said plurality of piezoelectric oscillators are arranged in an equi-spaced vertical stack.

According to a third aspect of the present invention, there is provided a computer program product executable by a programmable processing apparatus, comprising one or more software portions for performing the steps of the first or third aspects.

According to a fourth aspect of the present invention, there is provided a computer usable storage medium having a computer program product according to the fifth aspect stored thereon.

Embodiments of the present invention will now be described in detail with reference to the accompanying drawings, in which.

Figure 9:
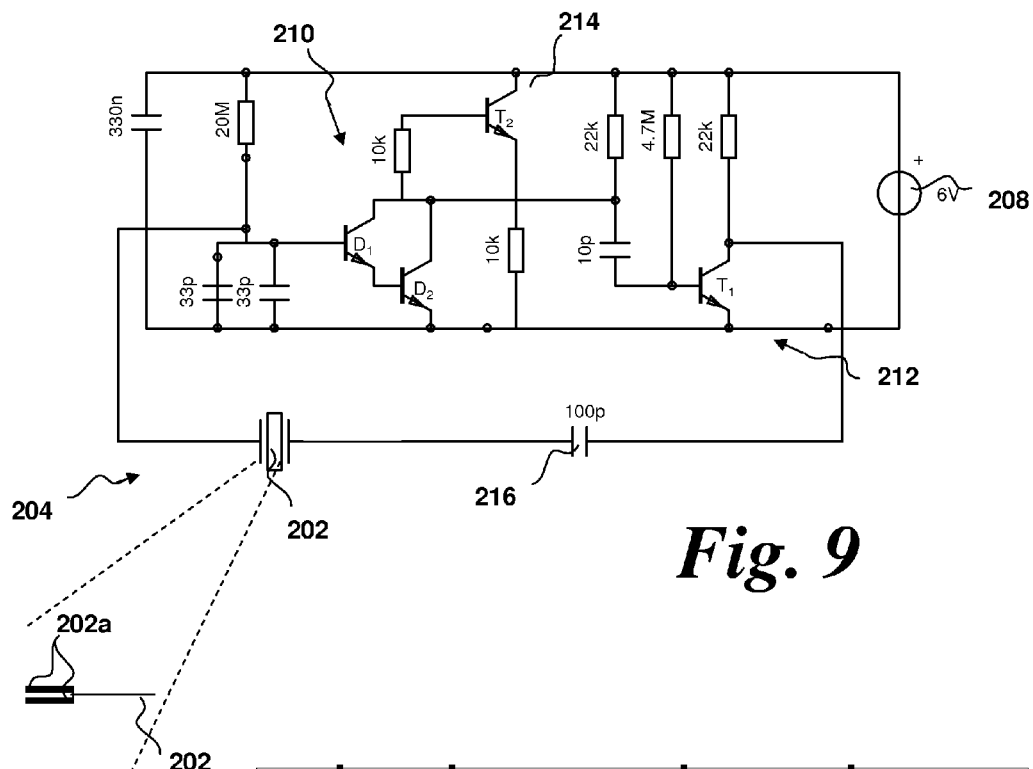
Figure 10:
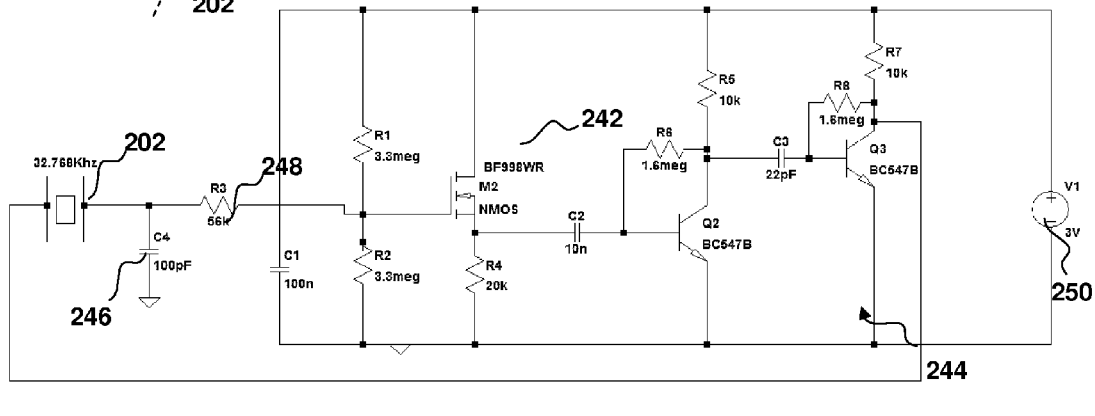
Figure 11:
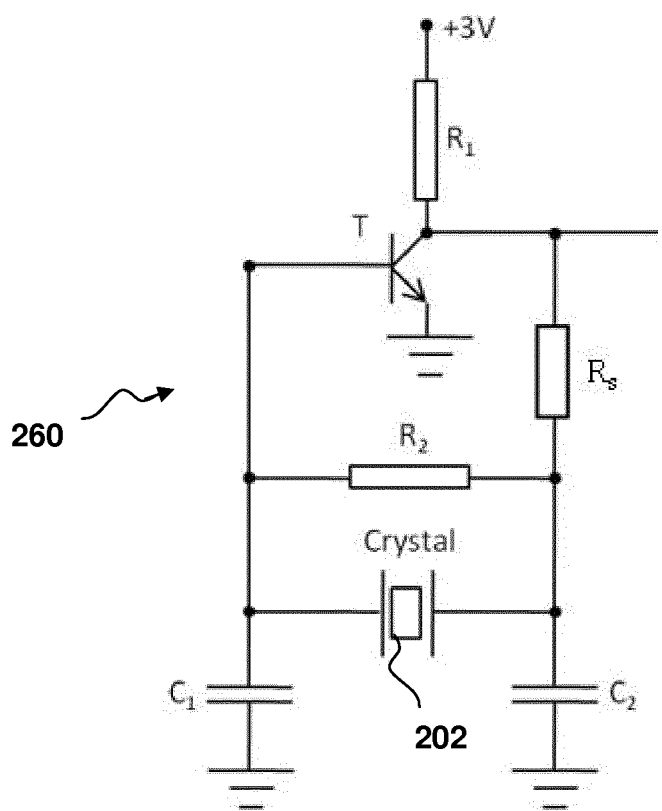
Figure 12:
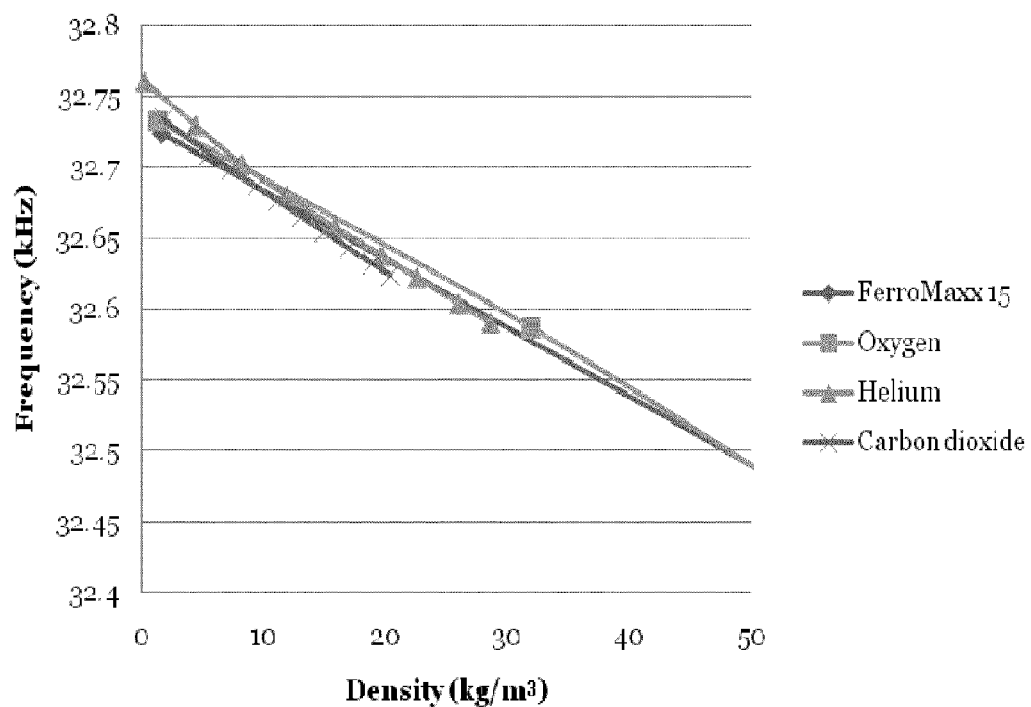
Figure 13:
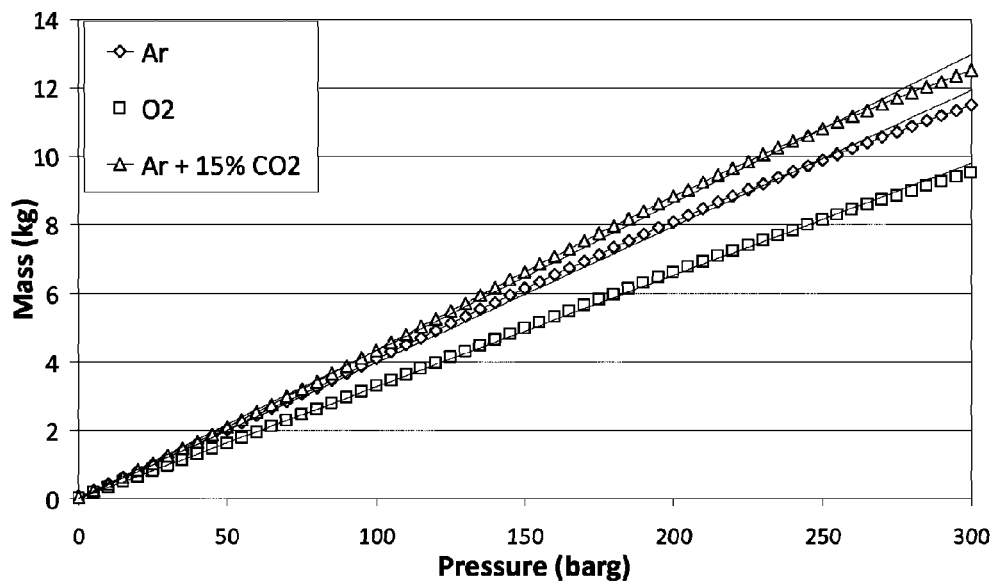
Figure 14:
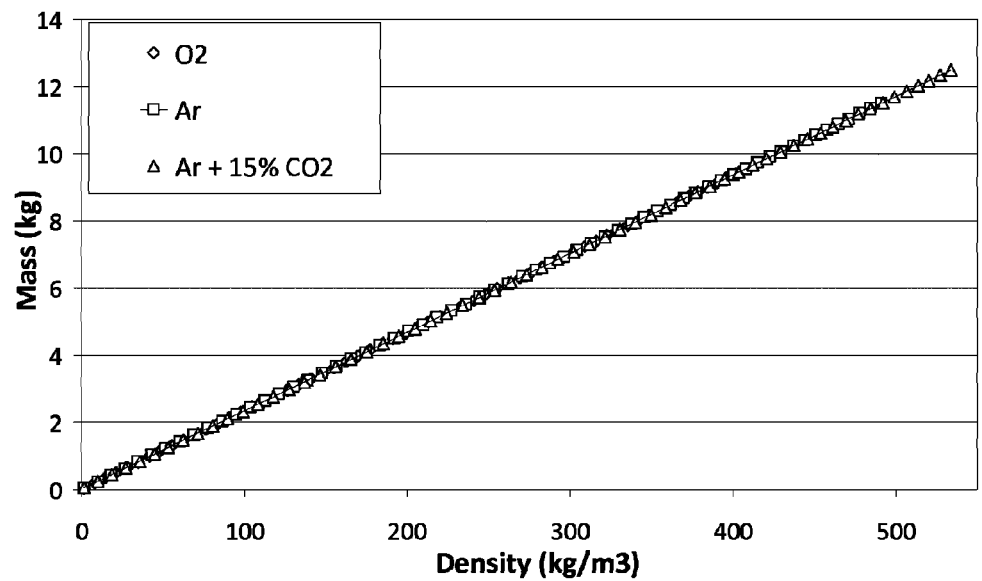
Figure 15:
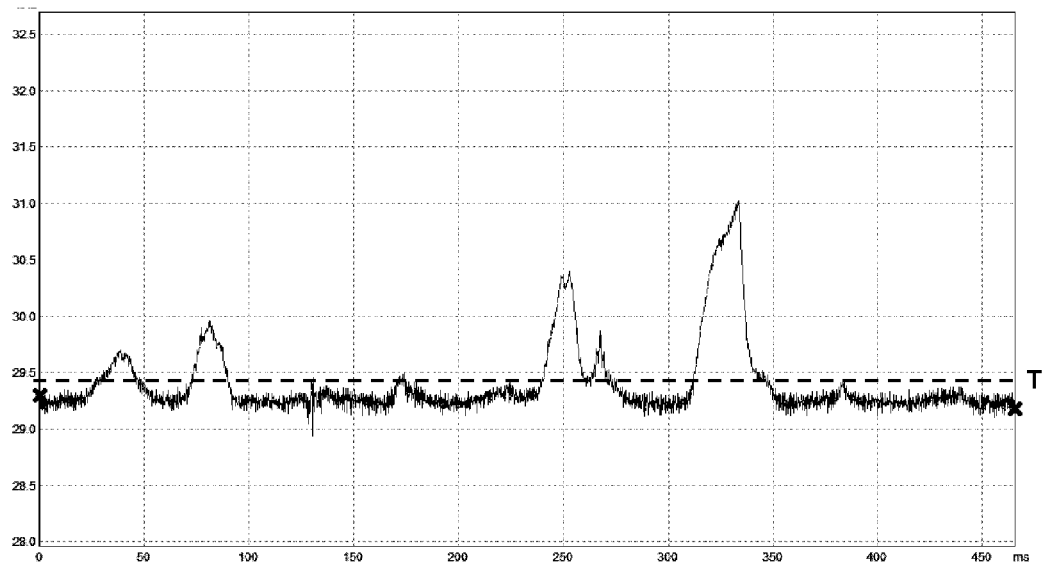
Figure 16:
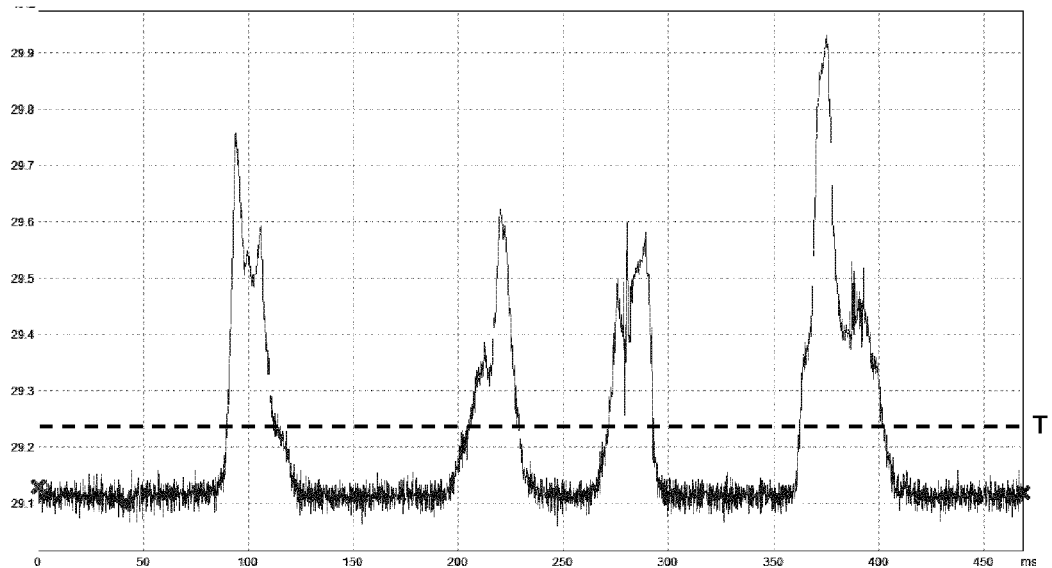
Figure 17:
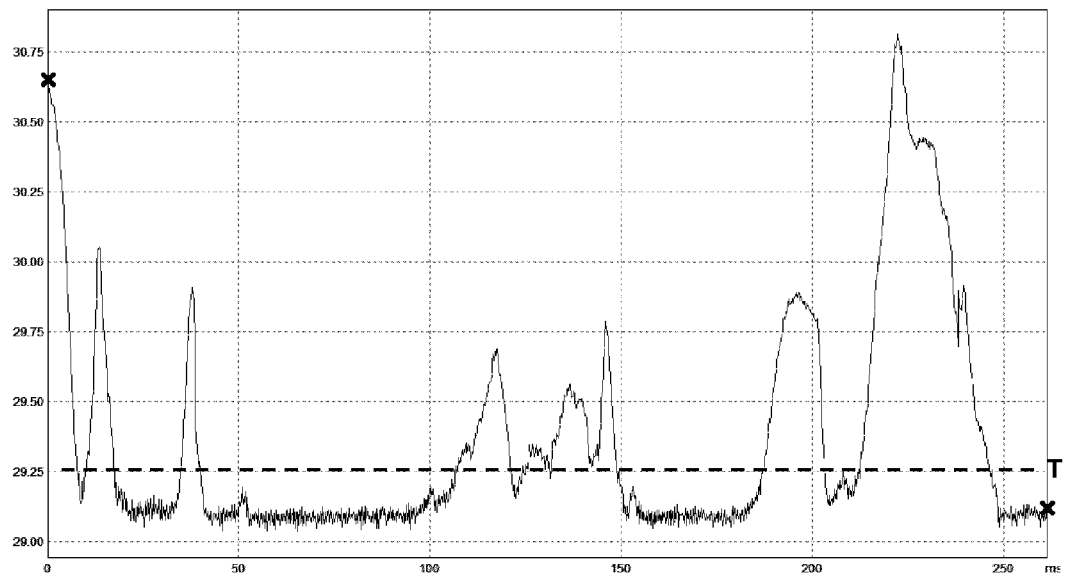
Figure 18:
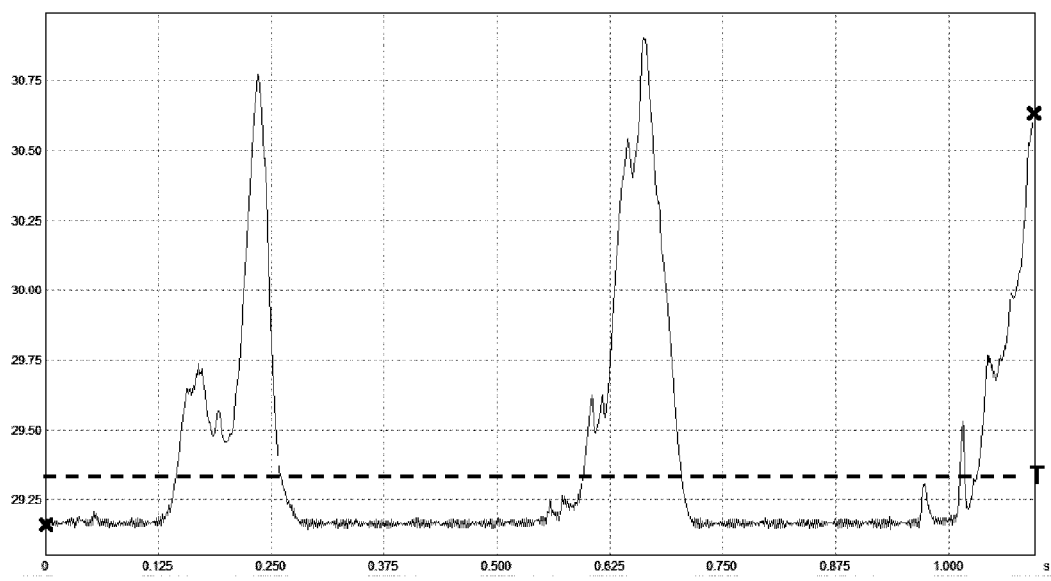
Figure 19:
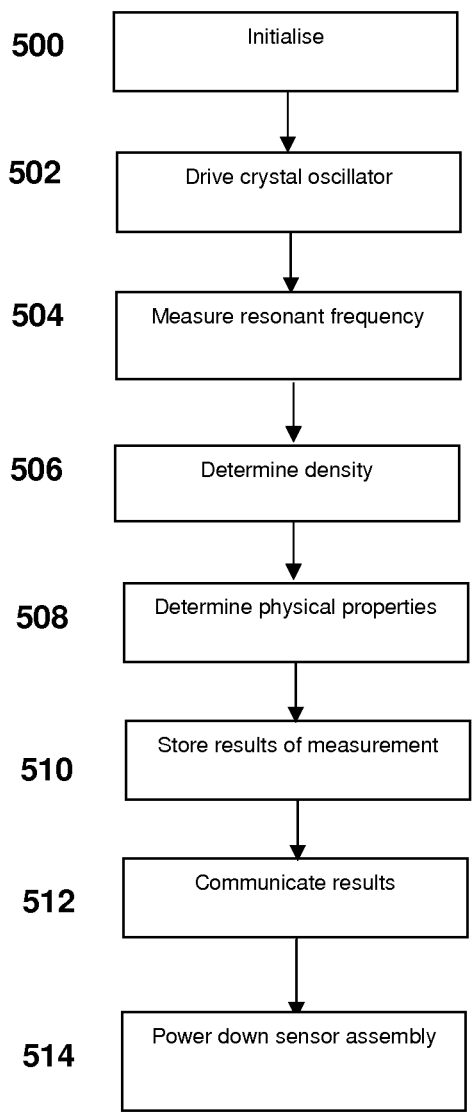
Figure 20:
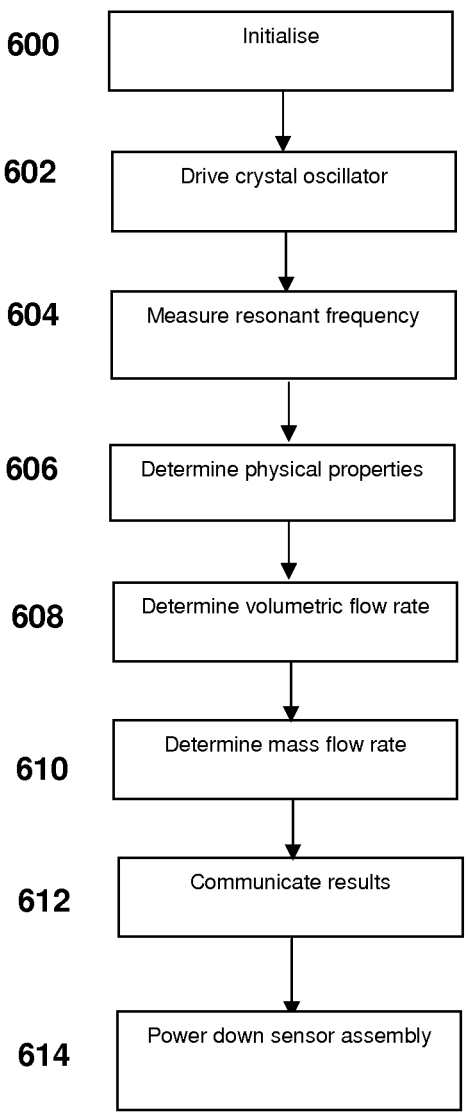
Figure 21:
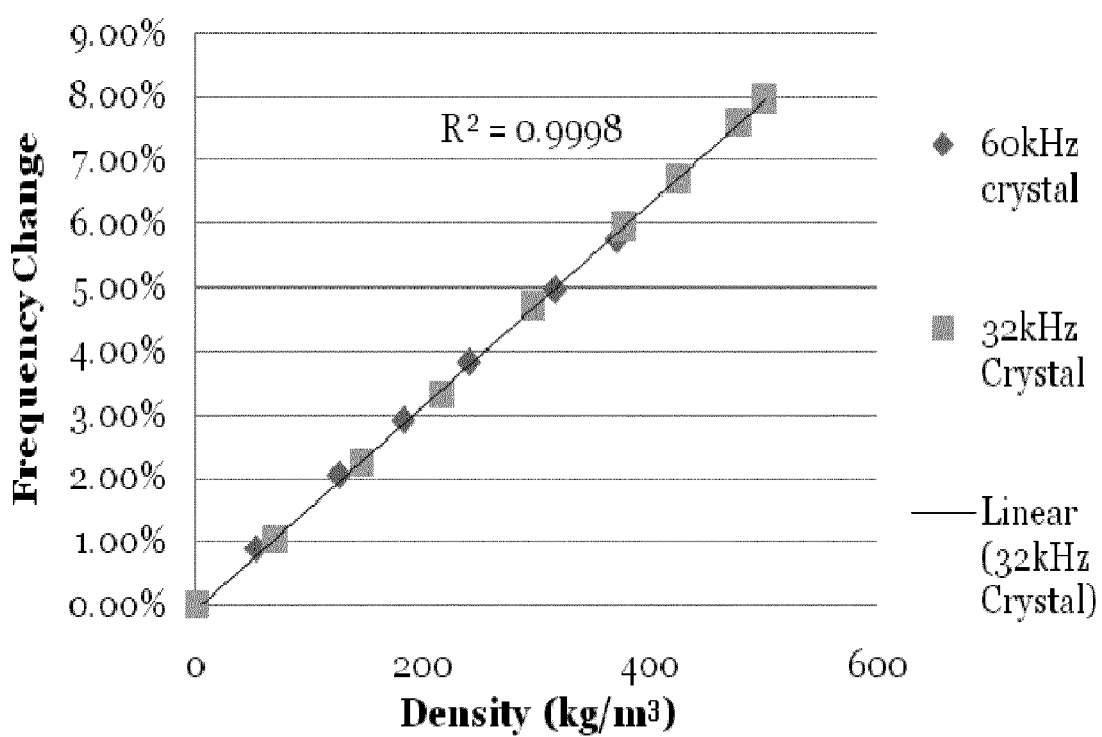
Figure 22:
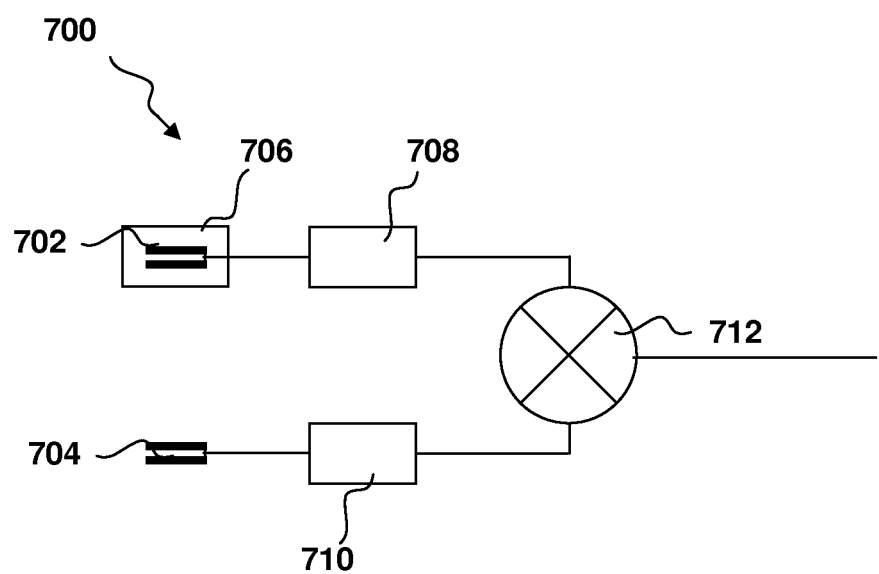
Figure 23:
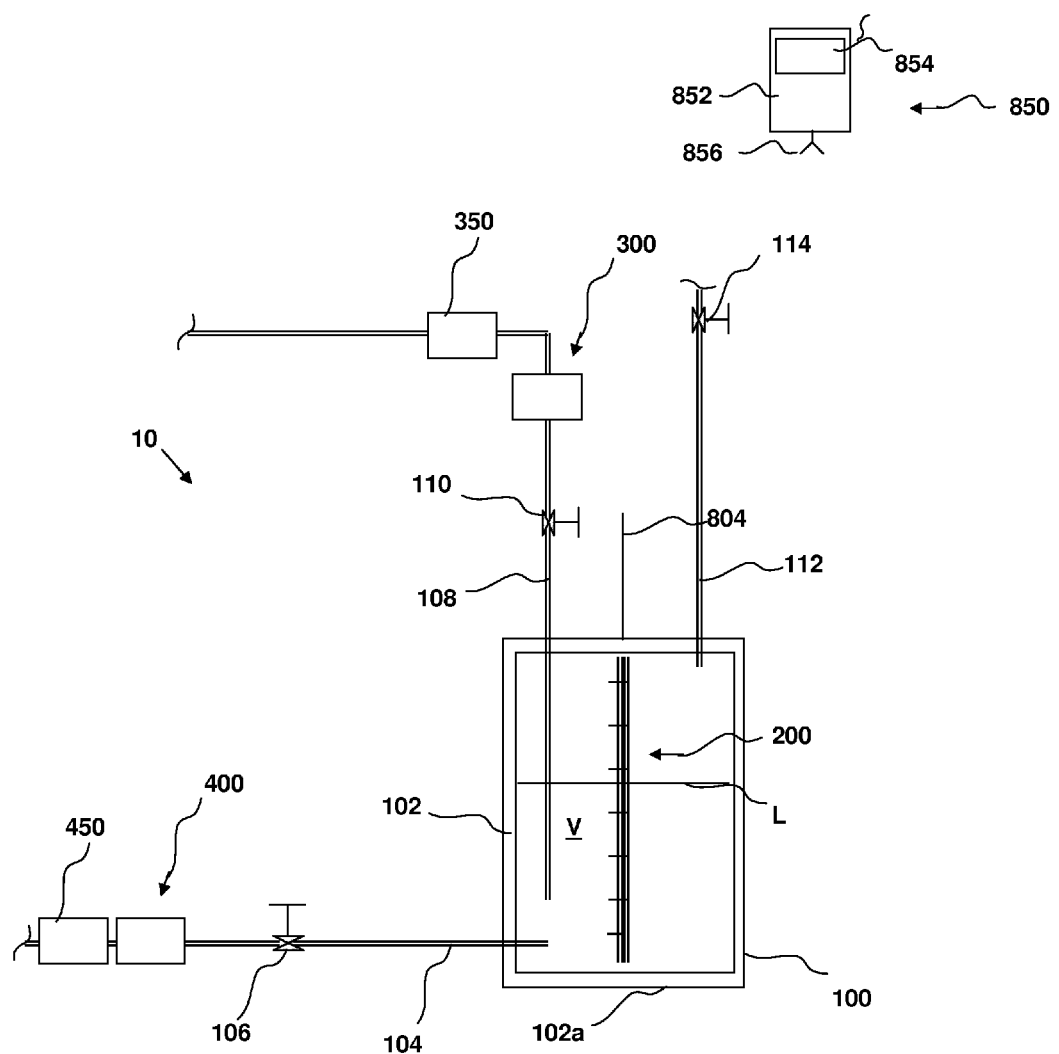

FIGS. 7a) to 7e) show different flow regimes in a vertical pipe;

FIGS. 8a) to 8f) show different flow regimes in a horizontal pipe;

FIG. 9 is a schematic diagram of a drive circuit for use with the first, second or third embodiments;

FIG. 10 is a schematic diagram showing an alternative drive circuit for use with the first, second or third embodiments;

FIG. 11 is a schematic diagram showing an alternative drive circuit for use with the first, second or third embodiments;

FIG. 12 shows a graph of quartz crystal frequency (kHz) on the Y-axis as a function of density (kg/m$^3$) for a number of different gases;

FIG. 13 shows a graph of gas mass (in kg) on the Y-axis as a function of pressure (bar g) on the X-axis for Argon, Oxygen and an Argon:Carbon Dioxide mixture;

FIG. 14 shows a graph of gas mass (in kg) on the Y-axis as a function of density (in kg/m$^3$) on the X-axis for the same three gases (Argon, Oxygen and an Argon:Carbon Dioxide mixture) as shown in FIG. 13;

FIG. 15 shows a graph of frequency (in kHz) on the Y-axis as a function of time (in milliseconds) on the X-axis for vigorously boiling liquid Nitrogen;

FIG. 16 shows a graph of frequency (in kHz) on the Y-axis as a function of time (in milliseconds) on the X-axis for slowly flowing liquid Nitrogen;

FIG. 17 shows a graph of frequency (in kHz) on the Y-axis as a function of time (in milliseconds) on the X-axis for faster flowing liquid Nitrogen;

FIG. 18 shows a graph of frequency (in kHz) on the Y-axis as a function of time (in seconds) on the X-axis for slugging liquid Nitrogen;

FIG. 19 is a flow chart illustrating a method according to a described embodiment;

FIG. 20 is a flow chart illustrating a method according to a described embodiment;

FIG. 21 shows a graph of the frequency behaviour of different crystal types;

FIG. 22 is a schematic diagram showing an alternative sensor assembly comprising two quartz crystals; and FIG. 23 shows an alternative arrangement using a remote electronic data unit.

Figure 1:
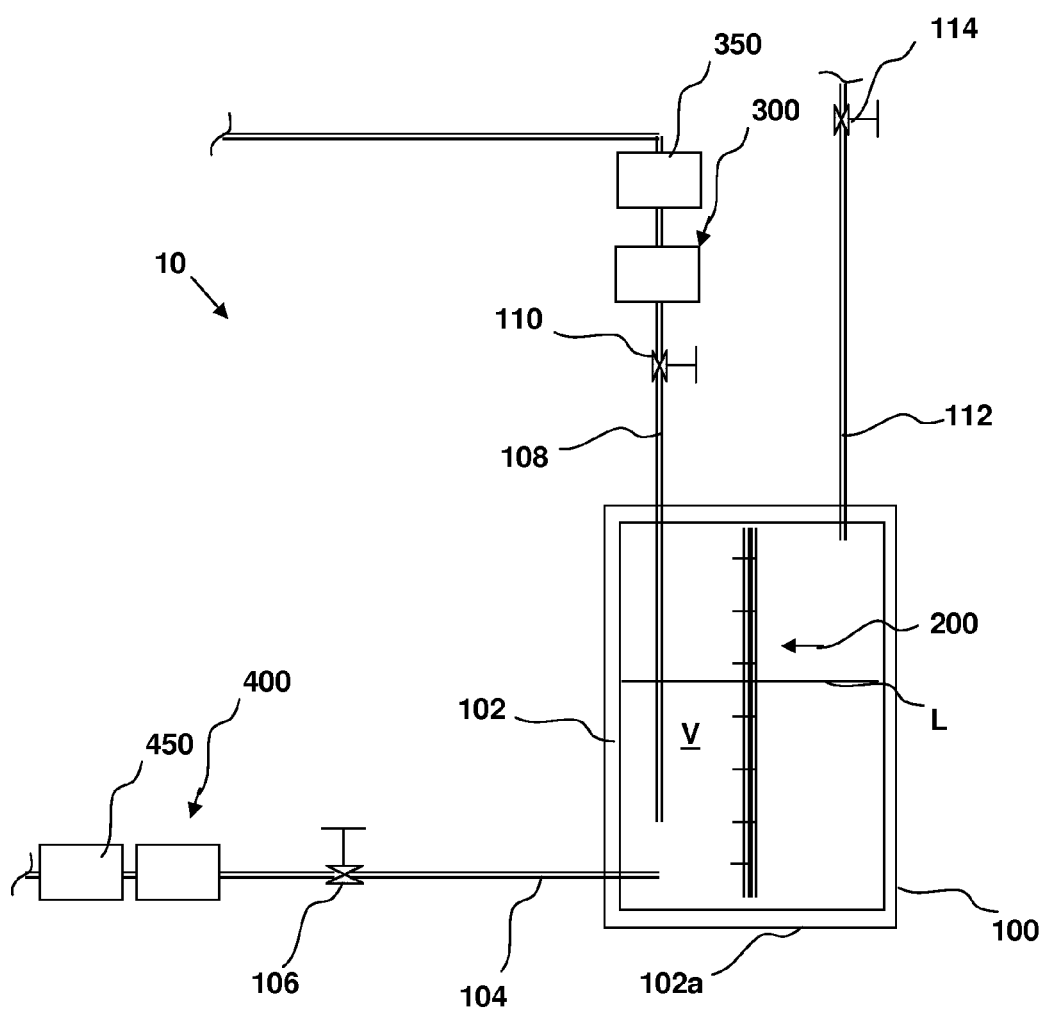
FIG. 1 is a schematic diagram of a cryogenic fluid system.

FIG. 1 shows a schematic view of a cryogenic fluid system 10 according to an embodiment of the invention.

The cryogenic fluid system 10 comprises a storage tank 100 having a tank body 102. The tank body 102 comprises a generally cylindrical container having a flat base 102a arranged to enable the storage tank 100 to stand unsupported on a flat surface. However, it is to be appreciated that the storage tank 100 may take other suitable forms; for example any suitable cryogenic storage vessel such as a portable vessel, a road tanker, a trailer, a chemical production facility, liquid air separation plant or combinations thereof.

Any suitable fluid may be contained within the cryogenic fluid system 10. However, a non-exhaustive list of suitable fluids may comprise: liquid Nitrogen; liquid Argon; liquid Hydrogen; liquid Helium; liquid Oxygen or mixtures thereof.

In this embodiment, the tank body 102 has a structure formed from steel, aluminium and/or composite materials. Vacuum insulation is provided within the walls to insulate the low temperature contents from the external environment. However, other types of suitable insulation may be utilised.

The storage tank 100 contains a volume of cryogenic fluid. The cryogenic fluid comprises a volume of cryogenic liquid having a fluid level L. Above the fluid level L exists a volume of gas or vapour. A first sensor assembly 200 is provided within the tank to measure the physical properties of the cryogenic fluid within the storage tank 100. The first sensor assembly 200 will be described later with reference to FIG. 2.

The storage tank 100 comprises three feed pipes 104, 108, 112. The pipe 104 is a liquid feed pipe and exits the storage tank body 102 at a point adjacent the base 102a. The pipe 104 is substantially horizontal and is operable to draw or supply cryogenic fluid from/to the storage tank 100 and comprises a valve 106. The valve 106 may be manually operable as shown and comprise a valve body which can be axially adjusted towards or away from a valve seat by means of rotation of a graspable handle selectively to open or to close the valve 106. Alternatively, the valve 106 may be automatically controlled by, for example, a solenoid valve.

The pipe 108 is also a liquid feed pipe and exits the storage tank body 102 at an upper end thereof. However, the pipe 108 extends into the tank body 102 by such a distance that the end of the pipe 108 is located below the liquid level L in the storage tank 100. The pipe 108 is operable to draw (via a pump or under top gas pressure) or supply cryogenic fluid from/to the storage tank 100 and comprises a valve 110. The valve 110 may be manually operable (as shown) or may be automatically controlled by, for example, a solenoid valve. At least a portion of the pipe 108 is arranged in a vertical configuration.

The pipes 104, 108 comprise insulated pipes and include vacuum jacketing or other insulating cladding to enable cryogenic liquids to be transported to/from the storage vessel 100.

A second sensor assembly 300 is located along a vertical section of the pipe 108. The second sensor assembly 300 will be described with reference to FIGS. 3 and 4. In addition, a volumetric flow meter 350 is located in the pipe 108 to measure the flow rate of the fluid as will be described later. The flow meter 350 may comprise any suitable arrangement; for example, a turbine to measure the flow rate of fluid.

A third sensor assembly 400 is located along a substantially horizontal section of the pipe 104. The third sensor assembly 400 will be described with reference to FIGS. 4 and 5. In addition, a volumetric flow meter 450 is located in the pipe 104 to measure the flow rate of the fluid therein as will be described later. The flow meter 450 may comprise any suitable arrangement; for example, a turbine to measure the flow rate of fluid.

The pipe 112 is a gas feed pipe and is arranged at an upper end of the storage tank 100. The end of pipe 112 is located above the liquid level L in the storage tank 100 and is arranged to enable venting of gas or vapours above the cryogenic liquid which may lead to excessive pressure within the storage tank 100. In this regard, the pipe 112 comprises a valve 114 to enable selective drawing of gas from the storage tank 100.

Figure 2:
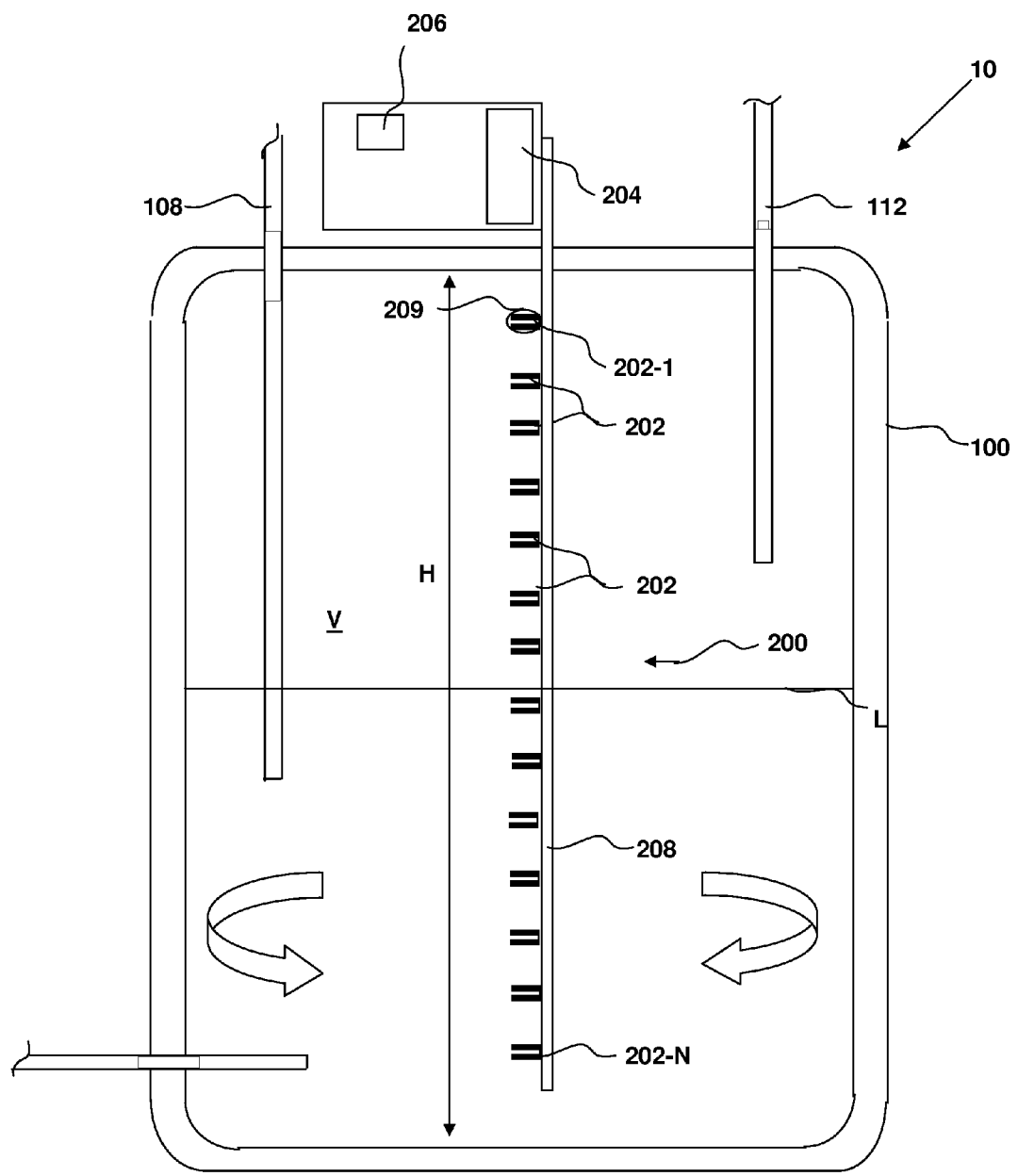
FIG. 2 is a schematic diagram showing a storage tank and sensor assembly according to a first embodiment of the invention.

The cryogenic fluid system 10 is provided with a first sensor assembly 200. The first sensor assembly 200 will be described with reference to FIG. 2. FIG. 2 shows a more detailed view of the interior of the storage tank 100.

The storage tank 100 has an internal volume V and a vertical internal height H (FIG. 2). In use, a proportion of the internal volume V is filled with cryogenic liquid which has a liquid level L. The first sensor assembly 200 is operable to measure, amongst other properties, the liquid level L.

The sensor assembly 200 is arranged to measure the density of the fluid at particular points of the internal height H of the storage tank 100. The sensor assembly 200 comprises a plurality of quartz crystal oscillators 202-1-202-N arranged in a vertical stack. Each quartz crystal oscillator 202 is connected to a respective drive circuit 204 by suitable wiring. Only a single drive circuit 204 is shown in FIG. 2. However, it is to be understood that a drive circuit 204 is provided for each quartz crystal oscillator 202. A processor 206 may also be provided, either separately or as part of the drive circuit 204. The sensor assembly 200 may be powered by a battery source or by an external power supply (e.g. a mains power connection). These details will be described later.

In the embodiment shown in FIG. 2, the quartz crystal oscillators 202-1 to 202-N are arranged on a vertical support structure 208 located within the internal volume V of the storage tank 100. In FIG. 2, fourteen quartz crystal oscillators 202-1 to 202-14 are shown (i.e. N=14). However, any other suitable number of oscillators could be used as required.

Each quartz crystal oscillator 202-1-202-N is arranged to act, in one aspect, as a level sensor and is operable to detect the density within the interior volume V of the storage tank 100 at a particular height of the storage tank 100. The quartz crystal sensors 202-1 to 202-N are equi-spaced along the support structure 208 in the direction of the interior vertical height H of the storage tank 100.

Each quartz crystal oscillator 202 comprises a small, thin section of cut quartz. Quartz demonstrates piezoelectric behaviour, i.e. the application of a voltage across the crystal causes the crystal to change shape, generating a mechanical force. Conversely, a mechanical force applied to the crystal produces an electrical charge.

Two parallel surfaces of the quartz crystal oscillator 202 are metallised in order to provide electrical connections across the bulk crystal. When a voltage is applied across the crystal by means of the metal contacts, the crystal changes shape. By application of an alternating voltage to the crystal, the crystal can be caused to oscillate.

The physical size and thickness of the quartz crystal determines the characteristic or resonant frequency of the quartz crystal. Indeed, the characteristic or resonant frequency of the crystal 202 is inversely proportional to the physical thickness between the two metallised surfaces. Quartz crystal oscillators are well known in the art and so the structure of the quartz crystal oscillator 202 will not be described further here.

The resonant vibration frequency of a quartz crystal will vary depending upon the environment in which the crystal is located. In a vacuum, the crystal will have a particular frequency. However, this frequency will change in different environments. For example, in a gas, the vibration of the crystal will be damped by the surrounding molecules of the fluid and this will affect the resonant frequency and the energy required to oscillate the crystal at a given amplitude. In a suitable liquid, the vibration will be further damped and the frequency of oscillation will change further.

Further, adsorption of gas or deposition of surrounding materials onto the crystal will affect the mass of the vibrating crystal, altering the resonant frequency. This forms the basis for commonly used selective gas analysers in which an absorbing layer is formed on the crystal and increases in mass as gas is absorbed onto the absorbing layer. However, in the present case, no coating is applied to the quartz crystal oscillator 202. Indeed, adsorption or deposition of material onto the quartz crystal oscillator 202 is undesirable in the present case since the accuracy of the measurement may be affected.

Therefore, it is generally considered that quartz crystal oscillators are unsuitable for use in liquids due to deposition of contaminants and fluid on the tines of the crystal oscillator. However, the inventors have found that, surprisingly, in the case of cryogenic liquids a quartz crystal oscillator provides an accurate measure of density without any contamination of the crystal which would lead to errors and inaccuracies.

The quartz crystal oscillator 202 of the present embodiment is tuning fork-shaped and comprises a pair of tines 202a (FIG. 9) approximately 5 mm long arranged to oscillate at a resonant frequency of 32.768 kHz. The tines 202a of the fork oscillate normally in their fundamental mode, in which they move synchronously towards and away from each other at the resonant frequency.

Additionally, it is desirable to use quartz which is AT cut or SC cut. In other words, a planar section of quartz is cut at particular selected angles so that the temperature coefficient of the oscillation frequency can be arranged to be parabolic with a wide peak at the desired operating temperature. Therefore, the crystal oscillator can be arranged such that the slope at top of the peak is precisely zero in the operating conditions required of it.

Such crystals are commonly available at relative low cost. In contrast to the majority of quartz crystal oscillators which are used in vacuo, in the present embodiment the quartz crystal oscillator 202 is exposed to the gas and liquid in the internal volume V of the storage tank 100.

Since the quartz crystal oscillators 202-1-202-N have a resonant frequency which is dependent upon the density of the surrounding fluid, the sensor assembly 200 is operable to detect which of the oscillators 202-1-202-N are immersed in the liquid cryogen and which are not. This enables identification of the level of liquid L in the storage tank 100.

Therefore, on a simple level, the plurality of quartz crystal oscillators 202-1-202-N are operable to provide an accurate indication of the level of liquid L in the storage tank 100 because of the difference in measured density between the cryogenic liquid and the gas or vapour in the storage tank 100.

In addition, the provision of the sensor assembly 200 enables more advanced parameters within the storage tank 100 to be monitored.

A problem which may occur within storage tanks such as storage tank 100 is that liquid convective circulation can lead to density stratification in single component liquids. In the absence of any continuous mechanical mixing of the single component liquid (e.g. the cryogenic liquid) intrinsic mechanisms of superheated wall boundary layer flow, incomplete evaporation at the surface, and a central downward jet of less superheated liquid, can lead to stratification into two layers.

Each stratified layer will be at a more or less uniform temperature but at a temperature different from the other layer. For example, a hotter, less dense layer may lie beneath a colder, denser layer.

The temperature difference across the liquid-liquid interface between the two layers is small, typically of the order of 0.1 to 1.0 K. Therefore, the mixing effect of thermally driven molecular diffusion in the absence of any convective motion is relatively small. Consequently, the associated density difference across the liquid-liquid interface acts so as to suppress local convective mixing and the stratification is therefore extremely stable.

However, if this state is maintained, the heating of the top layer by the wall boundary layer flow will continue. This will leading to either a continuing rise in temperature, an increase in thickness accompanied by a downward migration of the interface or a combination of the two.

When the density difference between the two layers becomes large enough, the superheated wall boundary layer flow in the denser, lower layer suddenly has insufficient buoyancy and inertia to penetrate the liquid-liquid interface. The boundary layer flow is trapped in the lower layer and no evaporation can take place to release the thermal energy contained within. Instead, the wall boundary layer turns over at the interface, and the kinetic energy and thermal energy contained therein is locked into the lower layer of liquid. This causes the lower layer of liquid to heat up instead.

When this happens, the evaporation rate will fall as the first indication of a stratification effect and associated increase in thermal overfill via the unstable superheated state. This type of thermal overfill in a single component liquid may be released by a violent nucleate boiling of the lower layer, with consequences such as the ejection of vapour mixed with liquid through the vents and possible mechanical damage to the storage vessel.

With a multi-component cryogenic liquid, the triggering and build-up of stratification can occur in a variety of ways, depending on the identity of the liquid components, and the previous history of the liquid elements. Once again, the stratification is convectively stable; but now mixing across the liquid-liquid interface is controlled by double diffusion, with both temperature and concentration gradients contributing to density-gradient driven, liquid convective mixing.

This stratification in a cryogenic liquid mixture inevitably leads to unstable evaporation, which has acquired the name "rollover". The unstable evaporation takes place when the stratified layers spontaneously mix, which can lead to a rapid increase in boil-off rate and hence tank pressure.

The sensor assembly 200 of the present invention is therefore, operable to detect these conditions, either through a different density gradient or profile through the internal height H of the storage tank 100, or through detection of gas bubbles resulting from boiling within the tank (since gas has a lower density than the surrounding liquid, this will be seen as a peak in the frequency response of a sensor). Experimental data relating to this will be described later.

In this embodiment, the drive circuits 204 are located outside the storage tank 100. Consequently, at least a part of the sensor assembly 200 is located externally of the storage tank 100. The quartz crystal oscillator 202 and the drive circuits 204 are connected by wiring which passes through a feed through (not shown). This arrangement protects any delicate electronic components from the extreme temperatures within the storage tank 100. However, the quartz crystal oscillator 202-1-202-N are constantly under isostatic pressure within the internal volume V of the storage tank 100 and, consequently, do not experience a pressure gradient. The benefits of internal location of the quartz crystal oscillators 202-1-202-N of the sensor assembly 200 are unique to solid state sensor devices such as the quartz crystal oscillator 202.

In an alternative embodiment, the whole of the sensor assembly 200 could be located within the storage tank 100. In this case, it would be necessary to provide appropriate shielding and/or insulation to protect at least some electronic components of the sensor assembly 200 from the extreme cold of cryogenic fluid within the storage tank 100.

In addition, a heating element 209 may be provided for one or more quartz crystal oscillators 202. Only one heating element 209 is shown in FIG. 2. The heating element 209 is applicable when, for example, the tank 100 is drained or the level L drops such that a sensor 202 is exposed to atmospheric air. In these conditions, condensation of water vapour and/or ice on the cold sensor 202 may lead to inaccuracies and errors in the sensor 202 reading, particularly if the sensor 202 is then plunged back into liquid cryogen. Therefore, the heater 209 is operable to evaporate any condensate or ice to prevent this.

Alternatively, the sensor assembly 200 may be connected to an antenna (not shown) for remote communication with, for example, a base station. This will be discussed later. In this case, the antenna may be located outside the storage tank 100 and connected to the sensor assembly 200 by means of a wire or equivalent connector. The antenna itself may be adapted and arranged to use any suitable communication protocol; for example, a non-exhaustive list may be RFID, Bluetooth, Infra red (IR), 802.11 wireless, frequency modulation (FM) transmission or a cell network.

Alternatively, one-wire communication may be implemented. One-wire communication needs only a single metallic conductor to communicate: the 'return' path of the circuit is provided by capacitive coupling through the air between the communicating devices. The skilled person would be readily aware of alternatives of the antenna (and associated transmission hardware) which could be used with the embodiments discussed herein.

Figure 3:
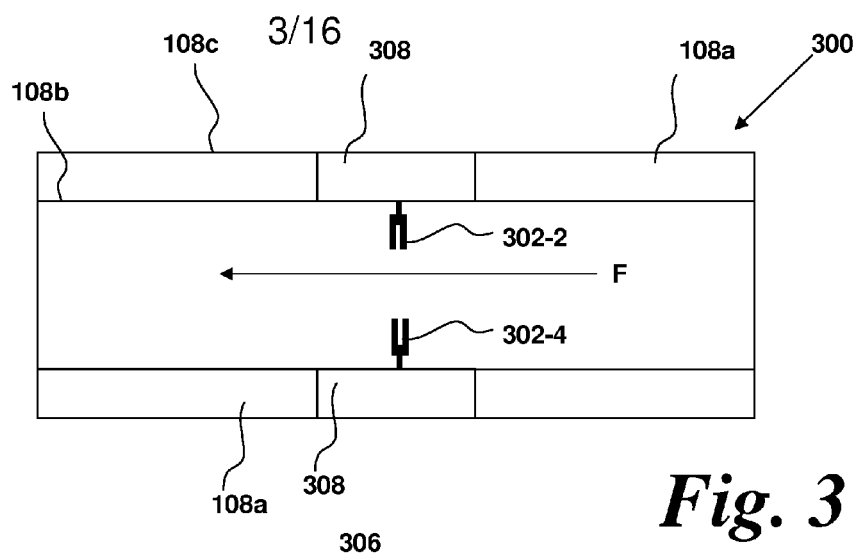
FIG. 3 is a schematic diagram showing a section through a vertical pipe and a sensor assembly according to a second embodiment of the invention.
Figure 4:
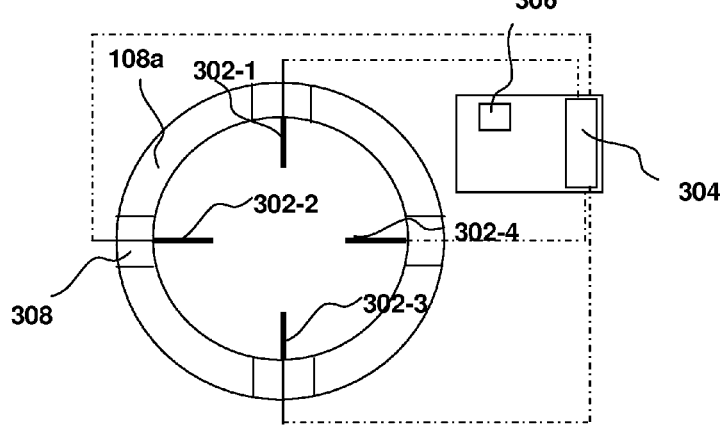
FIG. 4 is a cross section of the pipe and sensor assembly of FIG. 3.
Figure 5:
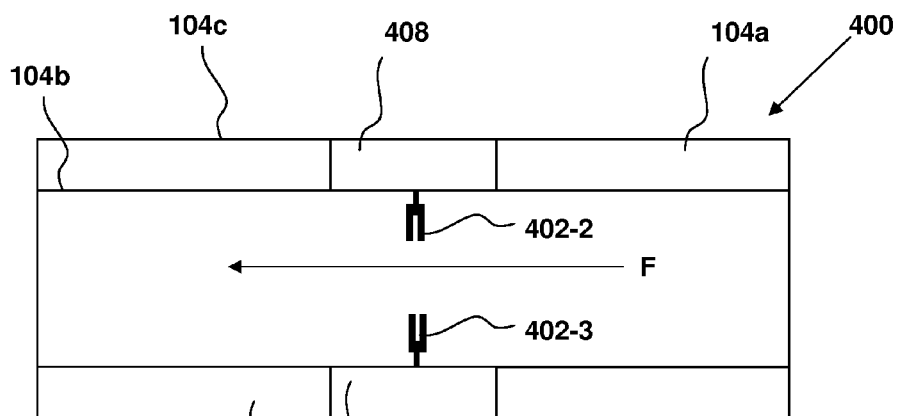
FIG. 5 is a schematic diagram showing a section through a horizontal pipe and a sensor assembly according to a third embodiment of the invention.

FIGS. 3 and 4 illustrate a second embodiment of the present invention in the form of a second sensor assembly 300. The second sensor assembly 300 is located in a substantially vertical section of the pipe 108. A plan section through the pipe 108 is shown in FIG. 5. The pipe 108 is shown in cross-section in FIG. 6. The pipe 108 is operable to transport cryogenic fluids and so comprises vacuum superinsulation 108a located between inner 108b and outer 108c walls of the pipe 108.

The third sensor assembly 300 comprises a plurality of quartz crystal oscillators 302-1 to 302-4. In this embodiment, four quartz crystal oscillators 302-1-302-4 are utilised. In this embodiment, the oscillators are arranged such that the long axis of each oscillator projects radially inwards towards the centre of the pipe 108 and perpendicular to the flow of fluid F (which, in FIG. 4, is out of the paper). The oscillators 302-1-302-4 are also equispaced around the interior circumference of the pipe 108.

However, the skilled person would be readily aware that other numbers and configurations of oscillators could be used as required. For example, an additional central oscillator could be located in the centre of the pipe 108 to provide five oscillators.

In common with the first embodiment, each quartz crystal oscillator 302 is connected to a respective drive circuit 304 by suitable wiring. Only a single drive circuit 304 is shown in FIG. 4. However, it is to be understood that a drive circuit 304 is provided for each quartz crystal oscillator 302. A processor 306 may also be provided, either separately or as part of a drive circuit 304. The sensor assembly 300 may be powered by a battery source or by an external power supply (e.g. a mains power connection). These details will be described later.

In order to provide electronic and physical connections between the drive circuits 304 and the quartz crystal oscillators 302-1 to 302-4, pass through insulators 308 are provided for each quartz crystal oscillator 302-1 to 302-4. Each pass through insulator 308 enables connecting wiring to pass through whilst maintaining a fluid-tight seal with sufficient insulation to enable cryogenic fluid to be transferred through the pipe 108.

Figure 6:
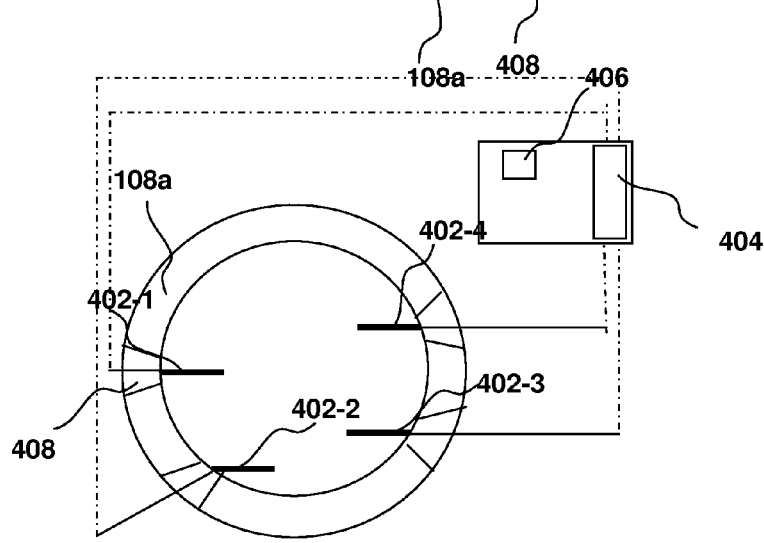
FIG. 6 is a cross section of the pipe and sensor assembly of FIG. 5.

FIGS. 5 and 6 illustrate a third embodiment of the present invention in the form of the third sensor assembly 400. The third sensor assembly 400 is located in a substantially horizontal section of the pipe 104. A plan section through the pipe 104 is shown in FIG. 5. The pipe 104 is shown in cross-section in FIG. 6. The pipe 104 is operable to transport cryogenic fluids and so comprises vacuum insulation 104a located between inner 104b and outer 104c walls of the pipe 104.

The third sensor assembly 400 comprises a plurality of quartz crystal oscillators 402-1 to 402-4. In this embodiment, four quartz crystal oscillators 402-1-402-4 are utilised. In this embodiment, the oscillators are arranged such that the long axis of each oscillator projects inwards towards the opposite side of the pipe 104 and perpendicular to the flow of fluid (which, in FIG. 6 is either into or out of the paper). The oscillators 402-1-402-4 are also arranged parallel to one another around the interior of the pipe 104.

In other words, the quartz crystal oscillators 402-1 to 402-4 are arranged parallel to one another such that the tines of each crystal oscillator lie flat to the oncoming flow F as shown in FIG. 5. As shown in FIG. 6, the quartz crystal oscillators 402-1 to 402-4 are arranged asymmetrically around the interior circumferential wall 104b of the pipe 104. In particular, one oscillator 402-2 is located adjacent the lower portion of the pipe 104. This is because, for a horizontal pipe, the effect of gravity may cause cryogenic liquid to flow along the bottom interior surface of the pipe, with gas above. By placing an oscillator at, or close to, the bottom of the pipe 104, this liquid cryogen can be measured directly.

In common with the first and second embodiments, each quartz crystal oscillator 402 is connected to a respective drive circuit 404 by suitable wiring. Only a single drive circuit 404 is shown in FIG. 4. However, it is to be understood that a drive circuit 404 is provided for each quartz crystal oscillator 402. A processor 406 may also be provided, either separately or as part of a drive circuit 404. The third sensor assembly 400 may be powered by a battery source or by an external power supply (e.g. a mains power connection). These details will be described later.

In order to provide electronic and physical connections between the drive circuits 404 and the quartz crystal oscillators 402-1 to 402-4, in common with the second embodiment, pass through insulators 408 are provided for each quartz crystal oscillator 402-1 to 402-4. Each pass through insulator 408 enables connecting wiring to pass through whilst maintaining a fluid-tight seal with sufficient insulation to enable cryogenic fluid to be transferred through the interior of the pipe 104.

The second and third embodiments of the present invention are operable to measure the physical properties of the flow of cryogenic fluids along vertical and/or horizontal pipes.

When a two-phase fluid (such as a cryogenic fluid) flows along a pipe, the flow will differ depending upon the proportion of the two phases in the fluid, the fluid pressure and the flow rate.

FIG. 7a) to e) shows diagrams illustrating the different flows of a two phase fluid which may occur along a vertical section of a pipe. When at very high quality, the flow is usually found to be in the bubbly flow regime as shown in FIG. 7a). This flow is characterized by discrete bubbles of vapour dispersed in a continuous liquid phase. In bubbly flow, the mean size of the bubbles is generally small compared to the diameter of the tube.

FIG. 7b) illustrates slug flow. This is where, at slightly lower qualities, smaller bubbles may coalesce into slugs that span almost the entire cross section of the pipe.

FIG. 7c) shows flow at intermediate qualities and lower flow rates, where the vapour shear on the liquid vapour interface may be near the value where it just balances the combined effects of the imposed pressure gradient and the downward gravitational body force on the liquid film. As a result, the liquid flow tends to be unstable and oscillatory. The vapour flow in the centre of the pipe flows continuously upward. Although the mean velocity of the liquid film is upward, the liquid experiences intermittent upward and downward motion. The flow for these conditions is highly agitated, resulting in a highly irregular interface. This oscillatory flow is referred to as churn flow.

FIGS. 7d) and 7e) show much lower quality of flow in which the two-phase flow generally assumes an annular configuration, with most of the liquid flowing along the wall of the pipe and the gas flowing in the central core. As shown in FIG. 7d), at intermediate qualities, one of two addition regimes may be observed. If both the liquid and vapor flow rates are high, an annular-type flow is observed with heavy "wisps" of entrained liquid flowing in the vapour core. Although this is a form of annular flow, it is sometimes designated as a separate regime, referred to as wispy annular flow. FIG. 7e) shows annular flow.

FIGS. 8a) to f) shows diagrams illustrating the different flows of a two phase fluid which may occur along a horizontal section of a pipe. One of the main differences between the regimes observed for horizontal flow and those for vertical flow is that there is often a tendency for stratification of the flow in horizontal pipes in which gravitational forces impose an asymmetry on the flow through the pipe. Regardless of the flow regime, the vapour tends to migrate toward the top of the tube while the lower portion of the channel carries more of the liquid.

FIG. 8a) illustrates very high quality, bubbly flow which is often observed for horizontal flow. However, as indicated the bubbles, because of their buoyancy, flow mainly in the upper portion of the tube.

FIG. 8b) illustrate the case where the quality of the flow is lower in the bubbly regime, coalescence of small bubbles produces larger plug-type bubbles, which flow in the upper portion of the tube. This is referred to as the plug flow regime.

FIG. 8c) shows that, at low flow rates and somewhat lower qualities, stratified flow may be observed in which liquid flowing in the bottom of the pipe is separated from vapor in the upper portion of the pipe by a relatively smooth interface.

FIG. 8d) shows a case where, if the flow rate is increased and/or the quality is decreased in the stratified flow regime, eventually the interface becomes unstable, whereupon the interface becomes wavy. This type of flow is categorized as wavy flow.

FIG. 8e) shows the case where, at high liquid flow rates, the amplitude of the waves may grow so that the crests span almost the entire width of the pipe, effectively forming large slug-type bubbles. Because of their buoyancy, the slugs of vapour flowing along the tube tend to skew toward the upper portion of the tube. In other respects it is identical to slug flow in vertical tubes, and hence it too is referred to as slug flow.

Finally, FIG. 8f) shows the situation where, at high vapour velocities and moderate liquid flow rates, annular flow is observed for horizontal gas-liquid flow. For such conditions, buoyancy effects may tend to thin the liquid film on the top portion of the tube wall and thicken it at the bottom.

The arrangements of the second and third embodiments are operable to detect the various flow mechanisms within a pipe. This can be done because of the marked difference between the resonant frequency of the quartz crystal oscillators 302, 402 when in liquid cryogen and when in gaseous cryogen. Furthermore, the fast response time of the quartz crystal oscillators 302, 402 enables classification of the flow within vertical and/or horizontal pipes to be performed as will be described later.

The structure of the drive circuit 204, 304, 404 will now be described with reference to FIG. 9. Whilst the following description relates to the drive circuit 204, it is to be understood that the following also applies to the drive circuits 304, 404.

The drive circuit 204 must meet a number of specific criteria. Firstly, the quartz crystal oscillator 202 of the present invention may be exposed to a range of fluid pressures; potentially, the pressures may vary from atmospheric pressure (when the storage tank 100 is empty) to being immersed in a dense liquid cryogen. Thus, the quartz crystal 202 is required to operate (and restart after a period of non-use) under a wide range of pressures and conditions.

Consequently, the quality (Q) factor of the quartz crystal oscillator 202 will vary considerably during use. The Q factor is a dimensionless parameter relating to the rate of damping of an oscillator or resonator. Equivalently, it may characterise the bandwidth of a resonator relative to its centre frequency.

In general, the higher the Q factor of an oscillator, the lower the rate of energy loss relative to the stored energy of the oscillator. In other words, the oscillations of a high Q factor oscillator reduce in amplitude more slowly in the absence of an external force. Sinusoidally driven resonators having higher Q factors resonate with greater amplitudes at the resonant frequency but have a smaller bandwidth of frequencies around that frequency for which they resonate.

The drive circuit 204 must be able to drive the quartz crystal oscillator 202 despite the changing Q factor. As the pressure in the storage tank 100 increases, the oscillation of the quartz crystal oscillator 202 will become increasingly damped, and the Q factor will fall. The falling Q factor requires a higher gain to be provided by an amplifier in the drive circuit 204. However, if too high an amplification is provided, the drive circuit 204, the response from the quartz crystal oscillator 202 may become difficult to distinguish. In this case, the drive circuit 204 may simply oscillate at an unrelated frequency, or at the frequency of a non-fundamental mode of the quartz crystal oscillator 202.

As a further limitation, the drive circuit 204 must be low power in order to run on small low power batteries for a long time with or without supplementary power such as photovoltaic cells.

The drive circuit 204 will now be described with reference to FIG. 9. In order to drive the quartz crystal oscillator 202, the drive circuit 204 essentially takes a voltage signal from the quartz crystal oscillator 202, amplifies it, and feeds that signal it back to the quartz crystal oscillator 202. The fundamental resonant frequency of the quartz crystal oscillator 202 is, in essence, a function of the rate of expansion and contraction of the quartz. This is determined in general by the cut and size of the crystal.

However, external factors also affect the resonant frequency. When the energy of the generated output frequencies matches the losses in the circuit, an oscillation can be sustained. The drive circuit 204 is arranged to detect and maintain this oscillation frequency. The frequency can then be measured by the processor 206, used to calculate the appropriate property of the gas required by the user and, if required, output to a suitable display means (as will be described later).

The drive circuit 204 is powered by a 6 V power source. The power source, in this embodiment, comprises a lithium ion battery. However, alternative power sources will be readily apparent to the person skilled in the art; for example, other battery types both rechargeable and non-rechargeable and a solar cell arrangement. In addition, mains electricity power may be used. This approach is particularly suitable for fixed storage tank installations.

The drive circuit 204 further comprises a Darlington pair Common Emitter amplifier 210. A Darlington pair comprises a compound structure consisting of two bipolar NPN transistors configured such that the current amplified by a first of the transistor is amplified further by the second one. This configuration enables a higher current gain to be obtained when compared to each transistor being taken separately. Alternative, PNP bipolar transistors may be used.

The Darlington pair 210 is arranged in a feedback configuration from a single transistor ($T_1$) Common Emitter amplifier 212. A NPN bipolar junction transistor is shown in FIG. 9. However, the skilled person would be aware of alternative transistor arrangements which may be used; for example, a bipolar junction PNP transistor or Metal Oxide Semiconductor Field Effect Transistors (MOSFETs).

The drive circuit 204 comprises a further NPN emitter follower transistor $T_2$ which acts as a buffer amplifier 214. The buffer amplifier 214 is arranged to function as a buffer between the circuit and the external environment.

A capacitor 216 is located in series with the quartz crystal oscillator 202. The capacitor 216, in this example, has a value of 100 pF and enables the drive circuit 204 to drive the quartz crystal oscillator 202 in situations where the crystal has become contaminated, for example by salts or other deposited materials.

An alternative drive circuit 240 will now be described with reference to FIG. 10. The drive circuit 240 may be used in place of the drive circuit 204 described above. In contrast to the drive circuit 204 described above, the drive circuit 240 includes a common drain Metal Oxide Semiconductor Field Effect Transistor (MOSFET) amplifier 242 in place of the Darlington pair of the circuit of FIG. 9. The MOSFET 242 functions as a high impedance input which enables the input impedance of the amplifier stage to be matched to the high impedance of the quartz crystal oscillator 202. In other words, the MOSFET 242 provides a unity gain with a high input impedance to reduce the electrical load on the quartz crystal oscillator 202.

The output of the common drain MOSFET amplifier 242 is fed to two successive single transistor (Q2,Q3) Common Emitter Amplifiers 244. Resistors R6 and R8 provide both negative feedback and biasing current for the transistors. The Common Emitter Amplifiers 244 provide a high gain to amplify the oscillations of the quartz crystal oscillator 202 and, in this embodiment, comprise NPN bipolar junction transistors. However, the skilled person would be aware of alternative transistor arrangements which may be used; for example, a bipolar junction PNP transistor or MOSFETs.

A capacitor 246 is connected between the quartz crystal oscillator 202 and ground. The capacitor 246, in this embodiment is operable to increase the drive to the quartz crystal oscillator 202.

A resistor 248 is connected in series with the quartz crystal oscillator 202. The resistor 248, in this embodiment, has a value of 56 kΩ and damps the oscillations of quartz crystal oscillator 202 in order to enable the circuit to oscillate over a wide range of pressures with only gradual changes in waveform.

The drive circuit 240 is powered by a 3 V battery 250. The battery 250, in this embodiment, comprises a lithium battery. However, alternative power sources will be readily apparent to the person skilled in the art; for example, other battery types both rechargeable and non-rechargeable and a solar cell arrangement. Alternatively, a mains supply arrangement may be used after DC rectification and appropriate voltage reduction.

An alternative drive circuit 260 will now be described with reference to FIG. 11. The drive circuit shown in FIG. 11 is configured similarly to a Pierce oscillator. Pierce oscillators are known from digital IC clock oscillators. In essence, the drive circuit 260 comprises a single digital inverter (in the form of a transistor) T, three resistors $R_1$, $R_2$ and $R_S$, two capacitors $C_1$, $C_2$, and the quartz crystal oscillator 202.

In this arrangement, the quartz crystal oscillator 202 functions as a highly selective filter element. Resistor $R_1$ acts as a load resistor for the transistor T. Resistor $R_2$ acts as a feedback resistor, biasing the inverter T in its linear region of operation. This effectively enables the inverter T to operate as a high gain inverting amplifier. Another resistor $R_S$ is used between the output of the inverter T and the quartz crystal oscillator 202 to limit the gain and to dampen undesired oscillations in the circuit.

The quartz crystal resonator 202, in combination with $C_1$ and $C_2$ forms a Pi network band-pass filter. This enables a 180 degree phase shift and a voltage gain from the output to input at approximately the resonant frequency of the quartz crystal oscillator. The above described drive circuit 260 is reliable and cheap to manufacture since it comprises relatively few components.

As discussed above, the sensor assembly 200 may include a processor 206 which receives inputs from the quartz crystal oscillator 202 and drive circuit 204. The processor 206 may comprise and suitable arrangement, such as an Application Specific Integrated Circuit (ASIC) or Field Programmable Gate Array (FPGA). The processor 206 is programmed to calculate, display and communicate parameters useful to users of the storage tank 100.

When used with the quartz crystal oscillator 202, the processor 206 may be configured to measure the frequency f or period of the signal from the drive circuit 204. This may be achieved by, for example, counting oscillations over a fixed time, and convert that frequency into a density value using an algorithm or look-up table. This value is passed to the processor 206 which is configured to perform, based on the supplied inputs, a calculation to determine the mass of the gas in the storage tank 100.

The processor 206 may, optionally, be designed for mass production to be identical in all storage tanks, with different features in the software and hardware enabled for different gases.

Additionally, the processor 206 may also be configured to minimise power consumption through implementation of standby or "sleep" modes which may cover the processor 206 and additional components such as the drive circuit 204 and quartz crystal oscillator 202.

Various schemes may be implemented; for example, the processor 206 may be on standby for 10 seconds out of every 11 seconds. Further, the processor 206 may control the quartz crystal oscillator 202 and drive circuit 204 such that these components are put on standby for the majority of time, only being switching the more power hungry components on for ½ second every 30 seconds. Alternatively or additionally, communication components such as an antenna can be switched off as required or used to activate the sensor assemblies 200, 300, 400.

The theory and operation of the first, second and third sensor assemblies 200, 300, 400 will now be described with reference to FIGS. 12 to 15.

The quartz crystal oscillator 202 has a resonant frequency which is dependent upon the density of the fluid in which it is located. Exposing an oscillating tuning fork-type crystal oscillator to a gas leads to a shift and damping of the resonant frequency of the crystal (when compared to the resonant frequency of the crystal in a vacuum). There are a number of reasons for this. Whilst there is a damping effect of the gas on the oscillations of the crystal, the gas adheres to the vibrating tines of the tuning fork crystal oscillator 202 which increases the mass of the oscillator. This leads to a reduction in the resonant frequency of the quartz crystal oscillator according to the motion of a one-sided, fixed elastic beam:

$$1)\ f = \frac{f_0}{\sqrt{1 + \frac{\rho}{M_0}}}$$

Where f is the frequency of oscillation, $f_0$ is the frequency of oscillation in a vacuum, p is the gas density, and $M_0$ is a constant.

The density ρ will in almost all cases be small compared to $M_0$, so that the formula can be approximated by the linear equation:

$$2)\ f = f_0\left(1 - \frac{\rho}{2M_0}\right)$$

which can re-expressed in terms of the frequency deviation Δf from $f_0$ as set out in equation 3):

$$3)\ \Delta f = 1/2\left(\frac{f_0}{M_0}\right)\rho$$

Consequently, to a good approximation, the change in frequency is proportional to the change in density of the gas to which the quartz crystal oscillator is exposed. FIG. 12 shows, for a number of different gases/gas mixtures, that the resonant frequency of the quartz crystal oscillator 202 varies linearly as a function of density.

In general, the sensitivity of the quartz crystal oscillator 202 is that a 5% change in frequency is seen with, for example, Oxygen gas (having Atomic mass number 32) at 250 bar when compared to atmospheric pressure.

The quartz crystal oscillator 202 is, surprisingly, particularly suitable for use as a density sensor for commercially-supplied fluids such as cryogenic fluids. Firstly, in order to sense accurately the density of a gas or liquid, it is necessary for the gas or liquid to be free from dust and other contaminants. This is generally the case with commercially supplied cryogenic fluids, but not with air, water, oil or in the generality of pressure monitoring situations.

Measurement of the physical properties of cryogenic two-phase fluids in this way has a number of advantages over known arrangements. For example, the density measured according to embodiments of the invention is corrected intrinsically for temperature. In contrast, the measurement of pressure using, for example, a Bourdon gauge varies proportionally with absolute temperature. Therefore, the present arrangement does not require temperature measurement and/or correction as is the case with known arrangements.

Further, the density of cryogenic gas or liquid measured according to an embodiment of the present invention is intrinsically corrected for compressibility Z. In a conventional arrangement, for example a Bourdon gauge, the compressibility of the gas needs to be corrected for. This is particularly important at high pressures, where the compressibility Z is not proportional to the gas pressure in the way expected of an ideal gas.

The automatic compensation for compressibility is illustrated with reference to FIGS. 13 and 14. FIG. 13 shows a graph of gas mass (in kg) on the Y-axis as a function of Pressure (bar g) for Argon, Oxygen and an Argon:Carbon Dioxide mixture. As shown in FIG. 13, the masses of the different gases vary with increasing pressure. Further, at high pressures in excess of 250 bar g, there is no longer a linear relationship between mass and pressure.

In embodiments of the present invention, the sensor assemblies 200, 300, 400 can be utilised to determine the density p as a function of time t and this information can be used to interpret conditions within the storage tank 100 (in the case of the first embodiment) and the flow of two-phase liquid along a pipe (in the case of the second and third embodiments).

Consider firstly the measurement of physical properties within the storage tank 100 by the first sensor assembly 200. As discussed above, the quartz crystal oscillators 202-1 to 202-N are operable to resonate at a frequency which is proportional to the density of the fluid in which they are immersed. Therefore, the array of oscillators 202-1 to 202-N provided in the first sensor assembly are operable to measure properties of the fluid within the storage tank 100 such as the liquid level and the density of the liquid at different heights within the storage tank 100. This assists in identification of stratification within the storage tank 100 as described above.

In addition, the fast response time of the quartz crystal oscillators 202-1 to 202-N and the markedly different resonant frequencies of the quartz crystal oscillators 202-1 to 202-N when in gas/vapour or liquid enables characterisation of the state of the fluid within the storage tank 100. In other words, it is possible to detect, using the first sensor assembly 200, whether the liquid within the storage tank 100 is boiling and, if so, how vigorously.

This can provide warning of potentially unsafe pressure build-ups within the storage tank 100, enabling corrective action (such as venting of excess gas or vapour) before structural damage occurs to the storage tank 100.

As described, in a two-phase fluid, gas bubbles will be present in the liquid within the storage tank 100. If the liquid is boiling, then the gas bubbles will rise towards the surface of the liquid and, consequently, will pass the quartz crystal oscillators 202-1 to 202-N. Therefore, by measuring the resonant frequency (which is proportional to density) as a function of time, as the gas bubbles pass each quartz crystal oscillator 202-1 to 202-N they can be detected.

Therefore, properties such as, non-exhaustively: the proportion of gas to liquid per unit time; the number of bubbles per unit time; and the size of the bubbles can be determined to provide an indication of the extent to which the liquid is boiling.

FIG. 15 illustrates an example of a measurement of the resonant frequency of a quartz crystal oscillator 202 in a tank of Liquid Nitrogen. FIG. 15 shows the resonant frequency (f) of the quartz crystal oscillator 202 (on the Y-axis) in KHz plotted as a function of time (on the X-axis) in milliseconds. The Liquid Nitrogen is boiling vigorously and this can be seen in FIG. 15 as peaks in the resonant frequency f as a function of time t.

As shown, the fast response of the quartz crystal oscillator 202 enables bubbles to be detected on the order of tens of milliseconds. However, when operating at very high speed, the quartz crystal oscillator 202 does not have time to stabilise fully in the new medium (i.e. the gas bubble as is passes through). Therefore, in some cases, a density figure obtained by the measured peak resonant frequency when in the gas bubble may not lead to an accurate density measurement. However, a quantitative analysis can be performed in order to determine characteristics of the fluid behaviour.

As shown in FIG. 15, a threshold level T can be identified. The threshold level T is a pre-defined level above which it is determined that a bubble has been detected. A system can then be implemented whereby the bubble frequency $f_b$ can be determined. In other words, the number of bubbles per unit time can be determined to identify conditions within the storage tank 100. The threshold value T may be set at any reasonable value which will exclude error variations in the resonant frequency of the liquid component, whilst detecting any gas bubbles.

Consider now the measurement and characterisation of two-phase fluid flow along horizontal and vertical pipes 104, 108 and measured using the second and third sensor assemblies 300, 400.

As described above with reference to FIGS. 7 and 8, the various flow states of two-phase fluids within horizontal and vertical pipes can be characterised by particular types of bubble formation. FIGS. 16 to 18 illustrate various flow situations as measured by the sensor assemblies 300, 400 in vertical pipes, although closely similar graphs are obtained for measurements on horizontal pipes.

FIG. 16 shows Liquid Nitrogen flowing through a Helium gas-filled pipeline at very slow flow rates. Helium gas is used so that a non-condensing gas is present within the gas bubbles. However, it will be appreciated that Nitrogen gas or other gases will also be present.

As shown, the flow is punctuated by gas bubbles which persist for approximately 50 ms on the quartz crystal oscillators 302, 402. These measurements may correspond to relatively annular flow such as that shown in FIGS. 7d) and 7e) for vertical pipes, and in FIGS. 8c), 8d) and 8f) for horizontal pipes.

FIG. 17 shows Liquid Nitrogen flowing through a Helium gas-filled pipeline at faster flow rates. As shown, the flow is less regular and irregular bubbles are detected by the quartz crystal oscillator 302, 402 which persist for variable amounts of time. This may correspond to more chaotic flow conditions within the pipe such as that shown in FIGS. 7a) and 7c) for vertical pipes, and in FIG. 8a) for horizontal pipes.

Finally, FIG. 18 shows Liquid Nitrogen flowing through a Helium gas-filled pipeline under conditions where slug flow occurs. The scale of FIG. 18 is longer than that of FIGS. 15 to 17 and the X-axis is in units of seconds.

As shown, the flow is highly regular and "slugs" of bubbles lasting for approximately 125 ms are detected by the quartz crystal oscillator 302, 402. The spacing between the "slugs" is also approximately constant. This may correspond to slug flow conditions within the pipe such as that shown in FIG. 7b) for vertical pipes, and in FIG. 8b) for horizontal pipes.

These measurements can be interpreted qualitatively as well as quantitatively. For example, the bubble frequency $f_b$ can be determined (i.e. the number of gas bubbles per unit time) and the size of the bubbles can be determined (i.e. how long the gas fraction persists on the quartz crystal oscillator 302, 402). This information can be used to determine the flow condition within the pipes 104, 108 as shown in FIGS. 7 and 8.

In addition, the measurements from the sensor assemblies 300, 400 can be used to provide information to assist control of other devices. For example, a cryogenic pump operable to pump liquid cryogen may reach an overspeed condition if exposed to a significant amount of gas within the two-phase liquid flow. Therefore, a sensor assembly 300, 400 located upstream of the pump inlet may be electronically connected to a pump controller such that, upon detection of a gas bubble, the pump motor could reduce speed to avoid an overspeed condition. Additionally, if a fluid flow contains a particular proportion of bubbles which may cause damage to the pump (e.g. cavitation), it is possible to detect this and to control the pump accordingly.

Alternatively, in the frozen food industry a cryogen spray nozzle is used to cryogenically freeze comestibles. The spray pattern from the spray nozzle will determine the extent and condition of the freezing applied to the comestibles. However, normal spray pattern will be disturbed by the presence of gas, and hence knowledge of the amount of gas present is important.

It is possible to calculate mass flow rate within a pipe using the above embodiments. As stated above, the quartz crystal oscillators 302, 402 do not generally have time to establish an accurate density for the gas bubbles before the gas bubbles pass the sensor. This is because a liquid such as a liquid cryogen (even one of very low viscosity) does not have sufficient time to drain from the oscillator 302, 402 before the bubble has passed. However, the inventors have found that the mass of gas within the gas bubbles can be ignored without unduly affecting the accuracy of the mass flow measurement.

In order to measure mass flow, it is necessary to determine, via the flow meter 350, 450, the volumetric flow rate (dV/dt) of the two-phase fluid. Then, using the sensor assembly 300, 400, the proportion of liquid to gas (B) and the liquid density (ρ) can be determined. The mass flow rate can then be calculated in accordance with equation 4)

4) $\frac{\partial M}{\partial t} = B\rho \frac{\partial V}{\partial t}$

A method according to an embodiment of the present invention will now be described with reference to FIG. 19. The method described below is applicable to the first embodiment described above with reference to FIGS. 1 and 2.

Step 500: Initialise Measurement

At step 500, the measurement of properties of the cryogenic fluid in the storage tank 100 is initialised. This may be activated by, for example, a user pressing a button on the outside of the storage tank 100. Alternatively, the measurement may be initiated by means of a remote connection, for example, a signal transmitted across a wireless network and received by the sensor assembly 200.

As a further alternative or addition, the sensor assembly 200 may be configured to initialise remotely or on a timer. The method proceeds to step 502.

Step 502: Drive the Quartz Crystal Oscillator

Once initialised, each drive circuit 204 is used to drive the respective quartz crystal oscillator 202. During initialisation, the respective drive circuit 204 applies a random noise AC voltage across the crystals 202-1 to 202-N. At least a portion of that random voltage will be at a suitable frequency to cause the crystal 202 to oscillate. The crystal 202 will then begin to oscillate in synchrony with that signal.

By means of the piezoelectric effect, the motion of the quartz crystal oscillator 202 will then generate a voltage in the resonant frequency band of the quartz crystal oscillator 202. The drive circuit 204 then amplifies the signal generated by the quartz crystal oscillator 202, such that the signals generated in the frequency band of the quartz crystal resonator 202 dominate the output of the drive circuit 204. The narrow resonance band of the quartz crystal filters out all the unwanted frequencies and the drive circuit 204 then drives the quartz crystal oscillator 202 at the fundamental resonant frequency f. Once the quartz crystal oscillator 202 has stabilised at a particular resonant frequency, the method proceeds to step 504.

Step 504: Measure Resonant Frequency of Quartz Crystal Oscillator

The resonant frequency f is dependent upon the conditions within storage tank 100. In the present embodiment, the change in resonant frequency Δf is proportional in magnitude to the change in density of gas or liquid within the storage tank 100 and will decrease with increasing density.

In order to make a measurement, the frequency of the quartz crystal oscillator 202 is measured for a period of approximately 1 s. This is to enable the reading to stabilise and for sufficient oscillations to be counted in order to determine an accurate measurement. The measurement of frequency is carried out in the processor 206. The processor 206 may also log the time, $T_1$, when the measurement was started.

Once the frequency has been measured, the method proceeds to step 506.

Step 506: Determine Density of Fluid

Once the frequency of each quartz crystal oscillator 202 has been measured satisfactorily in step 504, the processor 206 then calculates the density of the fluid at the level of that particular quartz crystal oscillator 202-1 to 202-N in the storage tank 100.

The method then proceeds to step 508.

Step 508: Determine Physical Properties of Fluid

In step 506, the density of fluid (either liquid or gas) at the height of each piezoelectric oscillator 202-1 to 202-N in the vertical stack is determined. This enables calculation of desired physical properties.

For example, the level of liquid within the storage tank 100 could be determined by identifying which oscillators 202-1 to 202-N are immersed in liquid and which are not.

Alternatively or additionally, the density of the liquid at different depths can be identified. This can be used to identify different layer densities and identify stratification which may lead to unsafe conditions in the tank.

Step 510: Store Results of Measurement

Once the densities or density gradients have been calculated, the respective density values could be simply recorded in an internal memory associated with the processor 206 of the sensor assembly 200 for later retrieval. As a yet further alternative, the data at time $T_1$ could be stored in a memory local to said processor 206.

The method then proceeds to step 512.

Step 512: Communicate Results

As an optional step, the physical parameters (e.g. fill level, tank stratification) can be displayed in a number of ways. For example, a screen attached to the storage tank 100 could display the mass of gas contained within the storage tank 100. In the alternative, the measurements could be communicated remotely to a base station or to a meter located on an adjacent fitting.

The method then proceeds to step 514.

Step 514: Power Down Sensor Assembly

It is not necessary to keep the sensor assembly 200 operational at all times. To the contrary, it is beneficial to reduce power consumption by switching the sensor assembly 200 off when not in use. This prolongs the life of the battery if utilised, or reduces energy consumption if connected to a mains supply.

The configuration of the drive circuit 204 enables the quartz crystal oscillator 202 to be restarted even if submerged in liquid within the storage tank 100. Therefore, the sensor assembly 200 can be shut down as and when required in order to save power.

A method according to another embodiment of the present invention will now be described with reference to FIG. 20. The method described below is applicable to the second and third embodiments described above with reference to FIGS. 1 and 3 to 6.

Step 600: Initialise Measurement

At step 600, the measurement of properties of the cryogenic fluid in a conduit such as pipe 104 or pipe 108. This may be activated by, for example, a user pressing a button on the outside of the respective sensor assembly 300, 400. Alternatively, the measurement may be initiated by means of a remote connection, for example, a signal transmitted across a wireless network and received by the respective sensor assembly 300, 400.

As a further alternative or addition, the sensor assembly 300, 400 may be configured to initialise remotely or on a timer. The method proceeds to step 602.

Step 602: Drive the Quartz Crystal Oscillator(s)

Once initialised, each drive circuit 304, 404 is used to drive the respective quartz crystal oscillator 302-1-302-4, 402-1-402-4. During initialisation, the respective drive circuit 304, 404 applies a random noise AC voltage across the crystals 302-1-302-4, 402-1-402-4. At least a portion of that random voltage will be at a suitable frequency to cause the crystal 302-1-302-4, 402-1-402-4 to oscillate. The crystal 302-1-302-4, 402-1-402-4 will then begin to oscillate in synchrony with that signal.

By means of the piezoelectric effect, the motion of the quartz crystal oscillator 302, 402 will then generate a voltage in the resonant frequency band of the quartz crystal oscillator 302, 402. The drive circuit 304, 404 then amplifies the signal generated by the quartz crystal oscillator 302, 402, such that the signals generated in the frequency band of the quartz crystal resonator 302, 402 dominate the output of the drive circuit 304, 404. The narrow resonance band of the quartz crystal filters out all the unwanted frequencies and the drive circuit 304, 404 then drives the quartz crystal oscillator 302, 402 at the fundamental resonant frequency f. Once the quartz crystal oscillator 302, 402 has stabilised at a particular resonant frequency, the method proceeds to step 604.

Step 604: Measure Resonant Frequency of Quartz Crystal Oscillators

The resonant frequency f is dependent upon the conditions within the conduit in which the sensor assembly 300, 400 is located. In the present embodiment, the change in resonant frequency Δf is proportional in magnitude to the change in density of gas or liquid within the storage tank 100 and will decrease with increasing density. Therefore, a marked change in density will be observed when the oscillators 302, 402 are exposed to the gas fraction of the two-phase fluid as opposed to the liquid fraction.

The measurement of frequency is carried out in the processor 306,406. The processor 306,406 may also log the time, $T_1$, when the measurement was started and may record measurements for a predetermined period thereafter.

Once the frequency has been measured, the method proceeds to step 606.

Step 606: Determine Physical Properties of Fluid

Once the frequency of each quartz crystal oscillator 302, 402 has been measured satisfactorily in step 604, the processor 306,406 then is operable to calculate desired parameters.

Each sensor assembly 300, 400 comprises, in the disclosed embodiments, four oscillators 302, 402. In order to obtain physical properties of the fluid under measurement, the processor 306, 406 may determine the average of the resonant frequencies of the four respective oscillators 302, 402. Alternatively, other processing or numerical methods may be used (such as weighted averages) or the four measurements may be used independently.

In one arrangement, the threshold level T can be utilised to detect when an oscillator 302, 402 is in a gas bubble. The threshold level T may be stored in the processor 306, 406 and may be manually inputted or may be obtained through a calibration process.

The processor 306, 406 can then log data regarding the time in which the oscillator 302, 402 is in gas and the time in which the oscillator 302, 402 is in liquid. After a predetermined measurement period (for example, of the order of seconds) the processor 306, 406 can determine the proportion of fluid which is gas and the proportion which is liquid. This may be determined as a percentage for use in the calculation set out in equation 4).

Alternatively or additionally, the pattern of gas bubbles may be monitored, and the bubble frequency and/or size may be logged by the processor 306, 406 in order to determine flow characteristics.

Alternatively or additionally, the processor 306, 406 may calculate the density of the liquid by utilising the liquid level frequency of the oscillators 302, 402.

The method then proceeds to step 608.

Step 608: Determine Volumetric Flow Rate

This step is optional and will only be carried out if mass flow rate is required. The flow meter 350, 450 is provided to measure volumetric flow rate. The flow meter 350, 450 comprises a turbine or other motive system which generates a signal proportional to the flow rate of the two-phase fluid. The volumetric flow rate is then communicated to the processor 306, 406.

The method proceeds to step 610.

Step 610: Determine Mass Flow Rate

Again, step 610 is optional and conditional on step 608 being carried out. In step 608, the volumetric flow rate is determined. In step 610, this information is utilised in the processor 306, 406, together with the liquid density measurement in step 606 and the proportion of gas to liquid in the two-phase fluid, to calculate the mass flow rate of the fluid in accordance with equation 4).

The method then proceeds to step 612.

Step 612: Communicate Results

As an optional step, the physical parameters (e.g. flow type, mass flow rate, liquid density) can be displayed in a number of ways. For example, a screen attached to the sensor assembly 300, 400 could display the relevant data. In the alternative, the measurements could be communicated remotely to a base station or to a meter located on an adjacent fitting.

The method then proceeds to step 614.

Step 614: Power Down Sensor Assembly

It is not necessary to keep the sensor assembly 300, 400 operational at all times. To the contrary, it is beneficial to reduce power consumption by switching the sensor assembly 300, 400 off when not in use. This prolongs the life of the battery if utilised, or reduces energy consumption if connected to a mains supply.

Variations of the above embodiments will be apparent to the skilled person. The precise configuration of hardware and software components may differ and still fall within the scope of the present invention. The skilled person would be readily aware of alternative configurations which could be used.

For example, the above described embodiments have utilised a quartz crystal oscillator having a fundamental frequency of 32.768 kHz. However, crystals operating at alternative frequencies may be used. For example, quartz crystal oscillators operating at 60 kHz and 100 kHz may be used with the embodiments described above. A graph showing the frequency change with density for different crystals is shown in FIG. 21. As a further example, a crystal oscillator operating at a frequency of 1.8 MHz could be used.

Higher frequency operation enables the pressure to be monitored more frequently because a shorter time period is required to sample a given number of cycles. Additionally, higher frequency crystals enable a smaller duty cycle to be used in a "sleep" mode of a crystal. By way of explanation, in most cases, the crystal and drive circuit will spend most of the time switched off, only being switched on for a second or so when a measurement is needed. This may occur, for example, once a minute. When a higher frequency crystal is used, the pressure can be measured faster. Therefore, the time in which the crystal is operational can be reduced. This may reduce power consumption and concomitantly improve battery life.

Additionally, the above embodiments have been described by measuring the absolute frequency of a quartz crystal oscillator. However, it may be advantageous to measure the shift in frequency of the sensor by comparing that frequency with a reference crystal of identical type but enclosed in a vacuum or pressure package. The pressure package may contain gas at a selected density, gas under atmospheric conditions or may be open to the atmosphere external of the storage tank 100.

A suitable sensor assembly 700 is shown in FIG. 22. The sensor assembly 700 comprises a first quartz crystal oscillator 702 and a second quartz crystal oscillator 704. The first quartz crystal oscillator 702 is a reference crystal which is located within a sealed container 706 under vacuum. The first quartz crystal oscillator 702 is driven by a drive circuit 708.

The second quartz crystal oscillator 704 is a crystal similar to the crystal 202 described in the earlier embodiments. The second quartz crystal oscillator 704 is exposed to the gas environment within the internal volume of the storage tank 100. The second quartz crystal oscillator 704 is driven by a drive circuit 710.

This comparison may be performed using an electronic mixer circuit 712 which combines the two frequency signal and produces an output at a frequency equal to the difference between the two crystals. This arrangement enables small changes due to, for example, temperature to be negated.

Further, the circuitry used in a storage tank 100 can be simplified because only the difference frequency is required to be measured. Further, this approach is particularly suitable for use with a high frequency (MHz) crystal oscillator, where it may be difficult to measure the crystal frequency directly.

Additionally, all of the electronics required to measure and display the density, mass or mass flow need not be mounted on or in the storage tank. For example, electronic functions could be split between units mounted on the storage tank permanently and units mounted on either a customer's usage station or temporarily mounted on the outlet of the storage tank such as the position normally used for a conventional flow meter.

An example of this arrangement is shown with reference to FIG. 23. The arrangement comprises a cryogenic fluid system 10 comprising a storage tank 100 and sensor assemblies 200, 300, 400 substantially as previously described with reference to previous embodiments.

In addition, an antenna 804 is provided for communication via any suitable remote communication protocol; for example, Bluetooth, Infra-red (IR) or RFID. Alternatively, one-wire communication may be utilised.

As a further alternative, acoustic communication methods may be used. The advantage of such methods is that remote communication can be effected without the requirement for an external antenna.

A display unit 850 is provided with a data unit 852. The data unit 852 comprises a display 854 and an antenna 856 for communication with the cryogenic fluid system 10. The display 854 may comprise, for example, an E-ink display to minimise power consumption and maximise visibility of the display. The data unit 852 may log various parameters as measured by the sensor assemblies 200, 300, 400.

Whilst the above embodiments have been described with reference to the use of a quartz crystal oscillator, the skilled person would be readily aware of alternative piezoelectric materials which could also be used. For example, a non-exhaustive list may include crystal oscillators comprising: lithium tantalate, lithium niobate, lithium borate, berlinite, gallium arsenide, lithium tetraborate, aluminium phosphate, bismuth germanium oxide, polycrystalline zirconium titanate ceramics, high-alumina ceramics, silicon-zinc oxide composite, or dipotassium tartrate.

Furthermore, whilst two-phase fluids have been illustrated above with regard to cryogenic fluids, other two-phase fluids are suitable for use with the present invention. For example, short chain hydrocarbons up to dodecane ($C_{12}H_{26}$) may be utilised.

Embodiments of the present invention have been described with particular reference to the examples illustrated. While specific examples are shown in the drawings and are herein described in detail, it should be understood, however, that the drawings and detailed description are not intended to limit the invention to the particular form disclosed. It will be appreciated that variations and modifications may be made to the examples described within the scope of the present invention.

The invention claimed is:

1. A method of measuring the physical properties of two-phase fluid flow using at least one piezoelectric oscillator immersed in the two-phase fluid, the two-phase fluid comprising a gas fraction and a liquid fraction dispersed within a particular volume of fluid, the method comprising:
   a) measuring the resonant frequency of the or each piezoelectric oscillator as a function of time; and
   b) determining, from the or each resonant frequency, whether the or each piezoelectric oscillator is immersed in a gas fraction or a liquid fraction and determining therefrom the proportion of the gas fraction to the liquid fraction as a function of time to characterise the two-phase fluid.

2. A method according to claim 1, further comprising comparing the resonant frequency with a pre-determined threshold frequency to determine whether said piezoelectric oscillator is immersed in a gas fraction or a liquid fraction.

3. A method according to claim 1, further comprising determining the density of at least the liquid component of the two-phase fluid.

4. A method according to claim 3, further comprising the steps of:
   c) measuring the volumetric flow rate of the fluid; and
   d) determining the mass flow rate of the two-phase fluid from the proportion of the gas fraction to the liquid fraction and from the density of the liquid fraction.

5. A method according to claim 1 further comprising determining the frequency of occurrence of at least one of a gas fraction and the size of a gas fraction.

6. A method according to claim 5, wherein the frequency of occurrence of at least one of a gas fraction and the size of a gas fraction is used to determine the flow regime of said two-phase fluid.

7. A method according to claim 5, wherein the frequency of occurrence of at least one of a gas fraction and the size of a gas fraction is used to determine whether said two-phase fluid is boiling.

8. A sensor assembly for measuring the physical properties of two-phase fluid flow comprising a gas fraction and a liquid fraction dispersed within a particular volume of fluid, the sensor assembly comprising at least one piezoelectric oscillator for immersion in the two phase fluid, the sensor assembly being arranged to measure the resonant frequency of the piezoelectric oscillator as a function of time, to determine, from the resonant frequency, whether the or each piezoelectric oscillator is immersed in a gas fraction or a liquid fraction and to determine therefrom the proportion of the gas fraction to the liquid fraction as a function of time to characterise the two-phase fluid.

9. A sensor assembly as claimed in claim 8, comprising a plurality of piezoelectric oscillators.

10. A sensor assembly according to claim 9, wherein said plurality of piezoelectric oscillators are arranged about the interior of a conduit through which said two-phase fluid is operable to flow.

11. A sensor assembly according to claim 8, further operable to determine whether the piezoelectric oscillator is immersed in a gas fraction or a liquid fraction by comparing the resonant frequency with a pre-determined threshold frequency.

12. A mass flow meter comprising the sensor assembly of claim 11, and a flow meter operable to determine the volumetric flow rate of the two-phase fluid, the mass flow meter being operable to determine the mass flow rate of the two-phase fluid from the proportion of the gas fraction to the liquid fraction and from a density of the liquid fraction.

13. A method according to claim 1 or sensor assembly according to claim 8, wherein the two-phase fluid is a cryogenic fluid.

\* \* \* \* \*